US011447523B2

(12) United States Patent
Szeto et al.

(10) Patent No.: US 11,447,523 B2
(45) Date of Patent: Sep. 20, 2022

(54) METHODS FOR REDUCING CD36 EXPRESSION

(71) Applicant: Cornell Research Foundation, Inc., Ithaca, NY (US)

(72) Inventors: Hazel H. Szeto, New York, NY (US); Shaoyi Liu, Palisades Park, NJ (US); Sunghee Cho, Scarsdale, NY (US)

(73) Assignee: CORNELL RESEARCH FOUNDATION, INC., Ithaca, NY (US)

( * ) Notice: Subject to any disclaimer, the term of this patent is extended or adjusted under 35 U.S.C. 154(b) by 0 days.

(21) Appl. No.: 16/838,290

(22) Filed: Apr. 2, 2020

(65) Prior Publication Data
US 2021/0047369 A1  Feb. 18, 2021

Related U.S. Application Data

(63) Continuation of application No. 16/140,325, filed on Sep. 24, 2018, now abandoned, which is a continuation of application No. 15/369,281, filed on Dec. 5, 2016, now abandoned, which is a continuation of application No. 14/285,226, filed on May 22, 2014, now abandoned, which is a continuation of application No. 14/075,686, filed on Nov. 8, 2013, now Pat. No. 9,150,614, which is a continuation of application No. 12/850,079, filed on Aug. 4, 2010, now Pat. No. 8,603,971, which is a continuation of application No. 12/434,216, filed on May 1, 2009, now Pat. No. 7,811,987, which is a continuation of application No. 11/532,764, filed on Sep. 18, 2006, now Pat. No. 7,541,340.

(60) Provisional application No. 60/718,170, filed on Sep. 16, 2005.

(51) Int. Cl.
| C07K 5/107 | (2006.01) |
| C07K 5/11 | (2006.01) |
| A61P 3/10 | (2006.01) |
| C07K 5/103 | (2006.01) |
| A61K 38/03 | (2006.01) |
| A61K 38/06 | (2006.01) |
| C07K 5/117 | (2006.01) |
| C07K 14/705 | (2006.01) |
| A61K 38/07 | (2006.01) |
| A61K 38/08 | (2019.01) |
| A61K 38/00 | (2006.01) |

(52) U.S. Cl.
CPC .............. *C07K 5/101* (2013.01); *A61K 38/03* (2013.01); *A61K 38/06* (2013.01); *A61K 38/07* (2013.01); *A61K 38/08* (2013.01); *A61P 3/10* (2018.01); *C07K 5/1008* (2013.01); *C07K 5/1016* (2013.01); *C07K 5/1019* (2013.01); *C07K 5/1024* (2013.01); *C07K 14/705* (2013.01); *A61K 38/00* (2013.01)

(58) Field of Classification Search
None
See application file for complete search history.

(56) References Cited

U.S. PATENT DOCUMENTS

| 4,522,811 A | 6/1985 | Eppstein et al. |
| 5,312,899 A | 5/1994 | Schiller |
| 5,602,100 A | 2/1997 | Brown et al. |
| 5,652,122 A | 7/1997 | Frankel et al. |
| 5,674,534 A | 10/1997 | Zale et al. |
| 5,716,644 A | 2/1998 | Zale et al. |
| 5,885,958 A | 3/1999 | Zadina et al. |
| 5,889,045 A | 3/1999 | Muller et al. |
| 5,993,848 A | 11/1999 | Suzuki et al. |
| 5,994,372 A | 11/1999 | Yaksh |
| 6,221,355 B1 | 4/2001 | Dowdy |

(Continued)

FOREIGN PATENT DOCUMENTS

| CA | 20002361364 | 9/2000 |
| EP | 1 712 125 | 10/2006 |

(Continued)

OTHER PUBLICATIONS

Guigas et al. "Metformin inhibits mitochondrial permeability transition and cell death: a pharmacological in vitro study," Biochem. J. (2004) 382, 877-884 (Year: 2004).*
Vincent et al. "Oxidative Stress in the Pathogenesis of Diabetic Neuropathy," Endocrine Reviews, 2004, 25(4):612-628 (Year: 2004).*
Beebe "Body Weight Issues in Preventing and Treating Type 2 Diabetes," Diabetes Spectrum vol. 16, No. 4, 2003, pp. 261-266 (Year: 2003).*
Aitman et al.,Identification of CD36 (Fat) as an insulin resistance gene causing defective fatty acid and glucose metabolism in hypertensive rats.
Alam, N.M et al., "A Novel Peptide (MTP-131) that Improves Mitochondrial Function Reverses Visual Decline in Mouse Models of Metabolic Dysfunction Leading to Diabetes," American Diabetes Association, (2012), Poster Presentation (1 page).

(Continued)

Primary Examiner — Christina Bradley
(74) Attorney, Agent, or Firm — Foley & Lardner LLP

(57) ABSTRACT

The invention provides a method for treating one or more complications of diabetes in a mammal. The method comprises administering to a mammal in need thereof an effective amount of an aromatic-cationic peptide having at least one net positive charge; a minimum of four amino acids; a maximum of about twenty amino acids; a relationship between the minimum number of net positive charges ($p_m$) and the total number of amino acid residues (r) wherein 3 $p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1.

4 Claims, 18 Drawing Sheets

(56) References Cited

U.S. PATENT DOCUMENTS

| | | | |
|---|---|---|---|
| 6,268,398 | B1 | 7/2001 | Ghosh et al. |
| 6,468,798 | B1 | 10/2002 | Debs et al. |
| 6,503,713 | B1 | 1/2003 | Rana |
| 6,703,483 | B1 | 3/2004 | Schiller |
| 6,759,520 | B1 | 7/2004 | Carr et al. |
| 6,900,178 | B2 | 5/2005 | Oeltgen et al. |
| 7,498,297 | B2 | 3/2009 | Szeto et al. |
| 7,541,430 | B2 | 6/2009 | Sensfuss et al. |
| 7,550,439 | B2 | 6/2009 | Szeto |
| 7,811,987 | B2 * | 10/2010 | Szeto .................. A61K 38/06 514/6.9 |
| 8,034,769 | B2 | 10/2011 | Kehrel et al. |
| 8,088,727 | B2 | 1/2012 | Neufer et al. |
| 8,603,971 | B2 * | 12/2013 | Szeto .................. A61P 25/00 514/6.9 |
| 8,940,696 | B2 | 1/2015 | Szeto et al. |
| 9,150,614 | B2 * | 10/2015 | Szeto .................. A61P 9/10 |
| 2004/0047861 | A1 | 3/2004 | Kehrel et al. |
| 2004/0248808 | A1 | 12/2004 | Szeto et al. |
| 2005/0096333 | A1 | 5/2005 | Dugar et al. |
| 2005/0158373 | A1 | 7/2005 | Szeto et al. |
| 2005/0192215 | A1 | 9/2005 | Ghosh et al. |
| 2006/0084606 | A1 * | 4/2006 | Szeto .................. A61P 25/00 514/1.4 |
| 2007/0015711 | A1 | 1/2007 | Szeto |
| 2007/0027070 | A1 | 2/2007 | Szeto et al. |
| 2007/0027087 | A1 | 2/2007 | Szeto et al. |
| 2007/0093969 | A1 | 4/2007 | Mendrick et al. |
| 2007/0129306 | A1 | 6/2007 | Szeto et al. |
| 2007/0259377 | A1 | 11/2007 | Urdea et al. |
| 2008/0014604 | A1 | 1/2008 | Devarajan et al. |
| 2008/0027082 | A1 | 1/2008 | Hocher et al. |
| 2008/0263683 | A1 | 10/2008 | Miyata et al. |
| 2009/0221514 | A1 | 9/2009 | Szeto et al. |
| 2009/0253641 | A1 | 10/2009 | Neufer et al. |
| 2009/0264369 | A1 | 10/2009 | Szeto et al. |
| 2010/0317571 | A1 | 12/2010 | Szeto et al. |
| 2013/0017150 | A1 | 1/2013 | Szeto et al. |
| 2014/0017033 | A1 | 1/2014 | Tsai |

FOREIGN PATENT DOCUMENTS

| | | | |
|---|---|---|---|
| JP | 10-158260 | | 6/1998 |
| JP | 2004-035510 A | | 2/2004 |
| JP | 2004-511526 | | 4/2004 |
| JP | 2007-521755 A | | 8/2007 |
| WO | WO-95/22557 | | 8/1995 |
| WO | WO-96/40073 A2 | | 12/1996 |
| WO | WO-99/15154 A1 | | 4/1999 |
| WO | WO-00/38651 A1 | | 7/2000 |
| WO | WO-00/55189 | | 9/2000 |
| WO | WO-02/05748 A2 | | 1/2002 |
| WO | WO-03/048326 A2 | | 6/2003 |
| WO | WO-2004/017986 A1 | | 3/2004 |
| WO | WO-2004/070054 A2 | | 8/2004 |
| WO | WO-2004070054 A2 * | 8/2004 | ............. A61P 43/00 |
| WO | WO-2004/075856 | | 9/2004 |
| WO | WO-2005/001023 | | 1/2005 |
| WO | WO-2004/070054 A3 | | 4/2005 |
| WO | WO-2005/032481 A2 | | 4/2005 |
| WO | WO-2005/044295 A1 | | 5/2005 |
| WO | WO-2005/055706 | | 6/2005 |
| WO | WO-2005/072295 A2 | | 8/2005 |
| WO | WO-2007/035640 A2 | | 3/2007 |

OTHER PUBLICATIONS

Alam, N.M et al., "Reducing Mitochondrial Oxidative Stress to Treat Diabetes and Age-related Visual Decline," Society of Neuroscience, (2011), Poster Presentation (1 page).

Alam, Nazia et al., "A novel Peptide that Improves Mitochondrial Function Reverses Diabetes- and Age-Related Visual Decline," American Aging Association, (2012), Abstract (1 page).

Anderson, Daniel C. et al., "Mitochondrial production of reactive oxygen species contributes to the β-adrenergic stimulation of mouse cardiomycytes," J. Physiol., Mar. 30, 2011, vol. 589, Issue 7, pp. 1791-1801.

Anderson, Ethan J. et al., "Mitochondrial H2O2 emission and cellular redox state link excess fat intake to insulin resistance in both rodents and humans",J. Clin. Invest., Feb. 2009, vol. 119, No. 3, pp. 573-581.

Azzouz, "Gene therapy for ALS: progress and prospects," Biochimical et Biophysica Acta, Nov. 2006, vol. 1762, pp. 1122-1127.

Berendsen, "A glimpse of the holy grail?" Science, Oct. 23, 1988, vol. 282, pp. 642-643.

Bickel et al., Synthesis and bioactivity of monobiotinylated DALDA: A Mu-specific opioid peptide designed for targeted brain delivery, J Pharmacol and Exp Therapeutics, 268(2): 791-796 (1994).

Bork et al., "Go hunting in sequence databases but watch out for the traps," Trends in Genetics, Oct. 1996, vol. 12, pp. 425-427.

Bork, "Powers and pitfalls in sequence analysis: the 70% hurdle," Genome Research, Apr. 2000, vol. 10, pp. 398-400.

Bradley et al., "Limits of cooperativity in a structurally modular protein: response of the notch ankyrin domain to analogous alanine substitutions in each repeat," Nov. 22, 2002, J. Mol. Biol., vol. 324, pp. 373-386.

Brenner, "Errors in genome annotation," Trends in Genetics, Apr. 1999, vol. 15, Issue 4, pp. 132-133.

Broekemeier et al., "Inhibition of the mitochondrial permeability transition by Cyclosporin A during long time frame experiments: Relationship between pore opening and the activity of mitochondrial phospholipases", Biochemistry, Dec. 19, 1995, vol. 34, pp. 16440-16449.

Brown, David A. et al., "Bendavia, a mitochondria-targeting peptide, reduces reperfusion injury and reactive oxygen species levels through a mechanism independent of direct oxygen radical scavenging: A multicenter study," American Heart Association, Nov. 20, 2012, vol. 126, Abstract (1 page).

Brown, David A., Ph.D., "Mitochondrial Derived Cardioprotection in Exercised Hearts: Role of Cardiac Glutathione," American College of Sports Medicine, (2012), DB Lab Presentation (28 pages).

Calkins, Marcus J. et al., "impaired mitocnonanai biogenesis, detective axonal transport or mitochondria, abnormal mitochondrial dynamics and synaptic degeneration in a mouse model of Alzheimer's disease," Hum. Mol. Genet., Dec. 1, 2011, vol. 20, No. 23, pp. 4515-4529.

Cao, Mingfeng et al., "Mitochondria-targeted antioxidant attenuates high glucose-induced P38 MAPK pathway activation in human neuroblastoma cells," Mol. Med. Report., Apr. 2012, vol. 5, Issue 4, pp. 929-993.

Carter, Edward A. et al., "Evaluation of the antioxidant peptide SS31 for treatment of burn-induced insulin resistance," Int. J. Mol. Med., Oct. 2011, vol. 28, Issue 4, pp. 589-594.

Chen, Min et al., "Mitochondria-targeted Peptide MTP-131 Alleviates Mitochondrial Dysfunction and Oxidative Damage in Human Trabecular Meshwork Cells," Invest. Ophthalmol. & Vis. Sci., Sep. 2011, vol. 52, No. 10, pp. 7027-7037.

Cho et al., "The Class B Scavenger Receptor CD36 Mediates Free Radical Production and Tissue Injury in Cerebral Ischemia," The Journal of Neuroscience, March 9, 20015, vol. 10, pp. 2504-2512.

Cho, et al., "A cell-permeable antioxidant peptide attenuates CD36-mediated ischemic injury via normalizing redox state", Neuroscience 2005 conference abstract, Presentation given Nov. 14, 2005, 1 page.

Cho, et al., "CD36: A multi-modal target for acute stroke therapy", Journal of Neurochemistry, (2009), vol. 109, Suppl. 1, pp. 126-132.

Cho, Janghyun et al., "Potent mitochondria-targeted peptides reduce myocardial infarction in rats," Coron. Artery Dis., May 2007, vol. 18, No. 3, pp. 215-220.

Cho, Sunghee et al., "A Novel Cell-permeable Antioxidant Peptide, SS31, Attenuates Ischemic Brain Injury by Down-regulating CD36,201D", J. Biol. Chem., Feb. 2007, vol. 282, No. 7, pp. 4634-4642.

Chonn et al., "Recent Advances in Liposomal Drug-Delivery Systems," Curr. Opin. Biotechnol., Dec. 1995, vol. 6, Issue 6, pp. 698-708.

(56) References Cited

OTHER PUBLICATIONS

Citron, "Alzheimer's Disease: Treatments in discovery and development," Nature Neuroscience Supplement, Nov. 2002, vol. 5, pp. 1055-1057.
Clapp III et al., "Cardiovascular and metabolic responses to two receptor-selective opioid agonists in pregnant sheep", Am. J. Obstet. Gynec., Feb. 1998, vol. 178, Issue 2, pp. 397-401.
Communication under Rule 71(3) EPC in EP Patent Application No. 06814862.2 dated Mar. 2, 2016 (46 pages).
Corpeleijn, et al.; "Direct association of a promoter polymorphism in the CD36/FAT fatty acid transporter gene with Type 2 diabetes mellitus and insulin resistance"; Diabetic Medicine (2006); vol. 23, pp. 907-911.
Dai, Dao-Fu et al., "Mitochondrial targeted antioxidant peptide ameliorates hypertensive cardiomyopathy," J. Am. Coll. Cardiol., Jun. 28, 2011, vol. 58, No. 1, pp. 73-82.
Decision of Reexamination in CN Patent Application No. 201410509385.4 dated Jan. 23, 2020 (with English translation) (12 pages).
Decision of Rejection in CN Patent Application 2014105093854 dated Feb. 11, 2018 (English translation only).
Demas, et al., "Anaesthesia for Heart Transplantation," Br. J. Anaesth., De. 1986, vol. 58, pp. 1357-1364.
Demers et al., "Identification of the growth hormone-releasing peptide binding site in CD36: a photoaffinity cross-linking study," Journal of Japanese Biochemical Soc, vol. 382, Jan. 1, 20014, pp. 417-424.
Dimaio et al., "Synthesis and pharmacological characterization in vitro of cyclic enkephalin analogues, Effect of Conformational Constraints on Opiate Receptor Selectivity," J. Med. Chem., Dec. 1, 1982, vol. 25, pp. 1432-1438.
Doerks et al., "Protein annotation: detective work for function prediction," Trends in Genetics, Jun. 1998, vol. 14, Issue 6, pp. 248-250.
Dooley, et al., "Selective ligands for the mu, delta and kappa opioid receptors identified from a single mixture based tetrapeptide positional scanning combinatorial library," Journal of Biological Chemistry, Jul. 24, 1998, vol. 273, Issue 30, pp. 18848-18856.
Drin et al., "Studies on the internationalization mechanism of cationic cell-penetrating peptides," Journal of Biological Chemistry, vol. 278, No. 33, pp. 31192-31201 (2003).
Eirin, Alfonso et al., "A Mitochondrial Permeability Transition Pore Inhibitor Improves Renal Outcomes After Revascularization in Experimental Atherosclerotic Renal Artery Stenosis," J. Am. Heart Assoc., Oct. 8, 2012, vol. 60, pp. 1242-1249; available at http://hyper.ahajournals.org/content/60/5/1242 and supplemental content available at http://hyper.ahajournals.org/content/suppl.2012/10/08/HYPERTENSIONAHA.112.199919.DC1.html (26 pages total).
Eirin, Alfonso et. al., "Chronic Treatment with Bendavia Preserves the Stenotic Kidney in Swine Atherosclerotic Renovascular Disease (ARVD)," American Society of Nephrology, (2012), Abstract & figures (2 pages).
Eirin, Alfonso et al., "Mitochondrial Targeted Peptides Attenuate Myocardial Damage after Renal Revascularization in Experimental Atherosclerotic Renovascular Hypertension," American Society of Nephrology, Aug. 2012, Abstract & figures (2 pages).
Eirin, Alfonso, et al., "MTP-131 reduces renal injury after percutaneous transluminal renal angioplasty (PTRA) in swine atherosclerotic renal artery stenosis (ARAS)," American Society of Nephrology, (2011), Poster Presentation (1 page).
European Search Report in EP Patent Application No. 06814864.2 dated Apr. 18, 2012 (12 pages).
Examination Report in AU Patent Application No. 2016203803, dated Dec. 6, 2016.
Examination Report in CA Patent Application No. 2947328 dated Oct. 13, 2017.
Examination Report in CA Patent Application No. 2947333 dated Oct. 19, 2017.
Examination Report in CA Patent Application No. 2947335 dated Oct. 16, 2017.
Examination Report in CA Patent Application No. 2947340 dated Oct. 19, 2017.
Examination report in CA patent Application No. 294/341 dated Oct. 12, 2017.
Examination Report in EP Patent Application No. 06814864.2 dated Nov. 19, 2013 (6 pages).
Examination report issued on Canadian Application 2947343, dated Oct. 24, 2017.
Examination Report No. 1 in AU Patent Application No. 2012202035 dated Feb. 12, 2013 (2 pages).
Examiner's First Report in AU Patent Application No. 2006292352 dated Jun. 2, 2011 (3 pages).
Examiner's Report in CA Patent Application No. 2,622,911 dated May 1, 2013 (4 pages).
Extended European Search Report in EP Patent Application No. 16176957.5 dated Oct. 14, 2016.
Extended Search Report in EP Patent Application No. 20167024.7 dated Jul. 8, 2020 (12 pages).
Farhangkhoee, H. et al., "Glucose-induced up-regulation of CD36 mediates oxidative stress and microvascular endothelial cell dysfunction," Diabetologia, (2005), vol. 48, pp. 1401-1410.
Final Office Action in U.S. Appl. No. 12/850,079 dated Feb. 27, 2013 (11 pages).
Final Office Action in U.S. Appl. No. 14/285,226 dated Jun. 8, 2016.
First Examination Report in AU Patent Application No. 2014203126 dated May 26, 2015 (4 pages).
First Office Action in CN Patent Application No. 200680040019.2 dated Aug. 6, 2010 (English translation only).
First Office Action in CN Patent Application No. 2013106271568 dated Oct. 24, 2014 (English translation only) (9 pages).
First Office Action in CN Patent Application No. 2014105093854 dated Nov. 6, 2015 (English translation only) (6 pages).
First Office Action in CN Patent Application No. 201610884213.4 dated Mar. 3, 2020 (with English translation) (17 pages).
Foreign Action other than Search Report on CN 201410509385.4 dated Apr. 4, 2019.
Foreign Action other than Search Report on KR 10-2019-0082102 dated Aug. 20, 2019.
Foreign Search Report on EP 19160103.8 dated Aug. 7, 2019.
Furuichi, et al., "Chemokine Receptor CX3CR1 Regulates Renal Interstitial Fibrosis after Ischemia-Reperfusion Injury," American Journal of Pathology, 169(2):372-387 (2006).
Geloen, et al., "CD36 Inhibitors Reduce Postprandial Hypertriglyceridemia and Protect against Diabetic Dyslipidemia and Atherosclerosis", PLoS One, (2012), vol. 7, No. 5, p. e37633.
Gilliam, Laura A.A. et al., "Doxorubicin acts via mitochondrial ROS to stimulate catabolism in C2C12 myotubes," Am. J. Physiol. Cell Physiol., Sep. 2011, vol. 302, Issue 1, pp. C195-C202.
Giunta, et al., "The leukocyte expression of CD36 is low in patients with Alzheimer's disease and mild cognitive impairment", Neurobiology of Aging, (2007), vol. 28, pp. 515-518, Elsevier.
Goilav, "Apoptosis in polycystic kidney disease," Biochimica et Biophysica Act, 1812:1272-2180 (2011).
Gregoriardis, "Engineering Liposomes for Drug Delivery: Progress and Problems," TIBTECH, Dec. 1995, vol. 13, pp. 527-537, 11 pages.
Guerrini et al., Opioid receptor selectivity alteration by single residue replacement: synthesis and activity profile of [Dmt] deltorphin B, European Journal of Pharmacology, Apr. 29, 1996, vol. 302 pp. 37-42, (abstract only.).
Habib, "Diabetes and renal tubular cell apoptosis," World Journal of Diabetes, 4(2): 27-30 (2013).
Hale, et al., "Context Dependent Role of the CD36-Thrombospondin-Histidine-Rich Glycoprotein Axis in Tumor Angiogenesis and Growth", PLoS One, (2012), vol. 7, No. 7, p. e40033.
Hale, Sharon L. et al., "A Novel Mitochondrial Permeability Transition Pore Inhibitor, Bendavia, Reduces, Microvascular Obstruction (No-Reflow) due to Myocardial Ischemia/Reperfusion Injury in the Rabbit," Basic Cardiovascular Sciences, (2011), Poster Presentation (1 page).

(56) References Cited

OTHER PUBLICATIONS

Han, Zhaosheng et al., "Mitochondria-Derived Reactive Oxygen Species Mediate Heme Oxygenase-1 Expression in Sheared Endothelial Cells"; J. Pharmacol. Exp. Ther., (2009), vol. 329, No. 1, pp. 94-101.
Heron-Milhavet, et al., "Muscle-Specific Overexpression ofCD36 Reverses the Insulin Resistance and Diabetes of MKR Mice", Endocrinology, (2004), vol. 145, No. 10, pp. 4667-4676.
Herve et al., "On the immunogenic properties of retro-inverso peptides. Total retro-inversion of t-cell epitopes causes a loss of binding to MHC II molecules," Molecular Immunology, Feb. 1997, vol. 34, Issue 2, pp. 157-163.
Holsey et al., "Cardiovascular effects of a µselective opioid agonist (Tyrosine-D-Arginine-Phenylalanine-Lysine-NH2) in fetal sheep; Sites and Mechanisms of Action," Am. J. Obstet. Gynecol., May 1999, vol. 180, Issue 5, pp. 1127-1130.
Hoye, et al., "Targeting Mitochondria", Accounts of Chemical Research, (2008), vol. 41, No. 1, pp. 87-97.
Imada et al., Effect of Edaravone on Renal Tubulointerstitial injury caused oy Unilateral Ureteral Obstruction in Rats, J Pharmacol Sci., vol. 97 Suppl. 1:97P (O-20026) (2005) (Abstract).
International Search Report and Written Opinion in International Application No. PCT/US2006/036291, dated Sep. 27, 2007.
Invitation pursuant to Article 94(3) and Rule 71(1) EPC in EP Patent Application No. 06814864.2 dated Sep. 2, 2015 (3 pages).
Kett et al., "Baroreflex-mediated bradycardia but not tachycardia is blunted peripherally by intravenous µ-opioid agonists," Am. J. Obstet. Gynecol., 178(5):950-955, 1998.
Kloner, Robert A. et al., "Reduction of Ischemia/Reperfusion Injury with Bendavia, a Mitochondria-Targeting Cytoprotective Peptide," J. Am. Heart Assoc., vol. 1, (2012), available at http://jaha.ahajournals.org/content/1/3/e001644 (14 pages).
Kloner, Robert A., et al., "Bendavia, A Novel Mitochondrial-Targeted Cytoprotective Compound Reduces Ischemia/Reperfusion Injury: Experience in 3 Independent Laboratories," American Heart Association, (2011), Abstract (2 pages).
Korczyn et al., "Emerging therapies in the pharmacological treatment of Parkinson's Disease," Drugs, vol. 62, Issue 5, pp. 775-786, 2002.
Kristian et al., "Calcium in Ischemic Cell Death," Stroke, 29(3), pp. 705-718, Mar. 1, 1998.
Kumar, et al., "Evidence of apoptosis in human diabetic kidney," Molecular and Cellular Biochemistry, 259:67-70 (2004).
Lasukova et al., "Activation of mu-opioid receptors and cardiomyocyte resistance to free radical damage," Patol Fiziol Eksp Ter., Apr.-Jun. 2001, vol. 2, pp. 15-17, English Abstract Only.
Lee, Hyung-yul et al., "Novel Mitochondria-Targeted Antioxidant Peptide Ameliorates Burn-Induced Apoptosis and Endoplasmic Reticulum Stress in the Skeletal Muscle of Mice," Shock, (2011), vol. 36, No. 6, pp. 580-585.
Li, Jianqiao et al., Mitochondria-targeted antioxidant peptide SS31 attenuates high glucose-induced injury on human retinal endothelial cells, Biochem. & Biophys. Res. Commun., (2011), 404, pp. 349-356.
Liang, XL., et al., "SS31 protects human RPE cells from oxidative damage and reduces laser-induced choroidal neovascularization," Association for Research in Vision and Opthamology, (2010), Poster Presentation (1 page).
Lichtenberg, D. et al., "Liposomes: Preparation, Characterization and Preservation," Methods of Biochemical Analysis, Mar. 16, 1988, vol. 33, pp. 337-462.
Lishmanov et al., "Ligands for opioid and o-receptors improve cardiac electrical stability in rat models of post-infarction cardiosclerosis and stress," Life Sciences, 65:13-17, 1999.
Liu, Shaoyi et al., "Boosting mitochondrial function to minimize ischemia-reperfusion injury," Experimental Biology, (2011), Poster Presentation (1 page).
Liu, Shaoyi et. al., "Mitochondria-targeting peptide (SS-31) promotes rapid repair of actin cytoskeleton following ischemia and protects tubular epithelial cell architecture," American Society of Nephrology, (2012), Abstract (2), (1 page).
Ma, Qi et al., "Superoxide Flashes: Early Mitochondrial Signals for Oxidative Stress-Induced Apoptosis," J. Biol. Chem., (Aug. 2011), vol. 286, No. 31, pp. 27573-27581.
Majer et al., "Synthesis of methylated phenylalanines via hydrogenolysis of corresponding 1,2,3,4-tetrahydroisoquinoline-3-caraboxylic acids," Int. J. Peptide Protein Res., 43:62-68, 1994.
Manczak, Maria et al., "Mitochondria-Targeted Antioxidants Protect Against Amyloid-β toxicity in Alzheimer's Disease Neurons," J. Alzheimer's Dis., (2010), 20, pp. S609-S631.
Marcinek, David J., et al., "Acute pharmacological intervention reverses mitochondrial deficits and improves function in aged skeletal muscle," American Aging Association, (2012), Abstract (1 page).
Margolis et al., "Diagnosis of Huntington Disease," Clinical Chemistry, 49(10):1726-1732, 2003.
Marleau, S., et al., "EP 80317, a ligand of the CD36 scavenger receptor, protects apolipoprotein E-deficient mice from developing atherosclerotic lesions", FASEB Journal, (2005), vol. 19, No. 13, pp. 1869-1871.
Merck Manual Online entry for Nephrotic Disease, Jan. 2010 (15 pages).
Min, Kisuk et al., "Mitochondrial-targeted antioxidants attenuate immobilization-induced skeletal muscle atrophy," Experimental Biology Meeting 2010, Anaheim CA, USA, Apr. 24-28, 2010, FASEB Journal, (2010) vol. 24: Abstract Ib670, (1 page).
Min, Kisuk et al., "Mitochondrial-targeted antioxidants protect skeletal muscle against immobilization-induced muscle atrophy," J. Appl. Physiol., (2011), 111(5), pp. 1459-1466.
Mizuguchi, et al., "Intratumor administration of fusogenic liposomes containing fragment A of diphtheria toxin suppresses tumor growth." Cancer Lett., Feb. 26, 1996, vol. 100, Issue 1, pp. 63-69.
Mizuguchi, Yasunori et al., "A novel cell-permeable antioxidant peptide decreases renal tubular apoptosis and damage in unilateral ureteral obstruction," Am. J. Physiol. Renal Physiol., (2008), 295, pp. F1545-F1553.
Moosmann, et al.; "Secretory Peptide Hormones Are Biochemical Antioxidants: Structure-Activity Relationship"; Mol. Pharmacol. (2002); vol. 61(2), pp. 260-268.
National Eye Institute "Facts About Diabetic Eye Disease" downloaded from https://www.nei.nih.gov/health/diabetic/retinopathy on Feb. 10, 2015, 9 pages.
Neilan et al., "Pharmacological characterization of the dermorphin analog [Dmt1]DALDA, a highly potent and selective u-opioid peptide," European Journal of Pharmacology, 419:15-23, 2001.
Ngo et al., "Computational complexity, protein structure prediction, and the leventhal paradox," The protein folding problem and tertiary structure prediction, (Ed. K. Mertz Jr. and S. Le Grand), Birkhauser Boston, 492-495, 1994.
Nieborowska-Skorska, Margaret et al., "Rac2-MRC-cIII-generated ROS cause genomic instability in chronic myeloid leukemia stem cells and primitive progenitors," Blood, (2012), vol. 119, No. 18, pp. 4253-4263.
Non-Final Office Action in U.S. Appl. No. 11/532,764 dated Aug. 7, 2008 (9 pages).
Non-Final Office Action in U.S. Appl. No. 12/850,079 dated Nov. 2, 2012 (24 pages).
Non-Final Office Action in U.S. Appl. No. 14/285,226 dated Mar. 18, 2015 (15 pages).
Non-Final Office Action in U.S. Appl. No. 16/140,325 dated Oct. 3, 2019.
Notice of Allowance in U.S. Appl. No. 11/532,764 dated Jan. 27, 2009 (16 pages).
Notice of Allowance in U.S. Appl. No. 12/434,216 dated Apr. 29, 2010 (15 pages).
Notice of Allowance in U.S. Appl. No. 12/850,079 dated Aug. 2, 2013 (15 pages).
Notice of Allowance in U.S. Appl. No. 14/075,686 dated Feb. 24, 2015, 8 pages.
Notice of Final Rejection in KR Patent Application No. 10-2008-7009150 dated Dec. 27, 2013 (English translation only) (3 pages).

(56) References Cited

OTHER PUBLICATIONS

Notice of Last Preliminary Rejection in KR Patent Application No. 2015-7000639 dated Feb. 11, 2016 (English translation only) (3 pages).
Notice of Preliminary Rejection in KR Patent Application No. 10-2016-0056491 dated May 23, 2016 (with English translation) (9 pages).
Notice of Preliminary Rejection in KR Patent Application No. 10-2016-0057030 dated May 23, 2016 (with English translation) (8 pages).
Office Action in JP Patent Application No. 2015-115856 dated Jun. 15, 2016 (English translation only) (2 pages).
Office Action in CA Patent Application No. 2,622,911 dated Feb. 24, 2015 (3 pages).
Office Action in CA Patent Application No. 2622911 dated Feb. 25, 2014 (3 pages).
Office Action in CN Patent Application No. 2014105093854 dated May 15, 2017.
Office Action in CN Patent Application No. 200680040019.2 dated Nov. 24, 2011 (English translation only).
Office Action in CN Patent Application No. 201210028972.2 dated Jun. 7, 2013 (English translation only) (9 pages).
Office Action in CN Patent Application No. 2014105093854 dated Aug. 24, 2016 (English translation only).
Office Action in CN Patent Application No. 2015101427348 dated Jul. 3, 2017 (English translation only).
Office Action in CN Patent Application No. 201510427348 dated May 18, 2018 (English translation only).
Office Action in JP Application No. 2008-531412 dated Feb. 20, 2012 (English translation only) (3 pages).
Office Action in JP Patent Application No. 2008-531412 dated Feb. 20, 2012.
Office Action in JP Patent Application No. 2012-181082 dated Feb. 9, 2015 (English translation only) (2 pages).
Office Action in JP Patent Application No. 2012-181082 dated Jan. 27, 2014 (English translation only) (3 pages).
Office Action in JP Patent Application No. 2013-006199 dated Feb. 9, 2015 (English translation only) (1 page).
Office Action in JP Patent Application No. 2013-006199 dated Mar. 24, 2014 (with English translation) (5 pages).
Office Action in JP Patent Application No. 2015-156656 dated Jul. 6, 2016 (English translation only) (1 page).
Office Action in JP Patent Application No. 2017-000444 dated Dec. 4, 2017.
Office Action in KR Patent Application No. 10-2015-7000639 dated Apr. 2, 2015 (English translation only) (2 pages).
Office Action in KR Patent Application No. 10-2015-7000640 dated Apr. 2, 2015 (English translation only) (2 pages).
Office Action in KR Patent Application No. 10-2016-0056491 dated Mar. 8, 2017.
Office Action in KR Patent Application No. 10-2016-0057030 dated Mar. 8, 2017.
Office Action in KR Patent Application No. 2008-7009150 dated May 13, 2013 (English translation only) (5 pages).
Office Action in KR Patent Application No. 2014-7007878 dated Jun. 3, 2014 (English translation only) (2 pages).
Office Action in KR Patent Application No. 2014-7007878 dated Oct. 9, 2014 (English translation only) (2 pages).
Office Action in KR Patent Application No. 2014-7021832 dated May 18, 2015 (English translation only) (2 pages).
Office Action in KR Patent Application No. 2014-7021832 dated Feb. 11, 2016 (2 pages).
Office Action in KR Patent Application No. 2014-7021832 dated Oct. 9, 2014 (English translation only) (3 pages).
Omoniyi et al., "A peripheral site of action for the attenuation of baroreflex-mediated bradycardia by intravenous μ-opioid agonists," Journal of Cardiovascular Pharmacolgy, 35(2):269-274, 2000.
Patel et al., "Pharmacotherapy of cognitive impairment in Alzheimer's Disease: A Review," J. Geriatr. Psychiatry Neurol., 8:81-95, 1995.
Petri, Susanne et al., "Cell-permeable peptide antioxidants as a novel therapeutic approach in a mouse model of amyotrophic lateral sclerosis", Journal of Neurochemistry, (2006), vol. 98, pp. 1141-1148.
Powers, Scott K et al., "Mitochondria-targeted antioxidants protect against mechanical-ventilation-induced diaphragm weakness," Crit. Care Med., (2011), vol. 39, No. 7, pp. 1749-1759.
Preliminary Rejection in KR Patent Application No. 2015-7000639 dated Nov. 29, 2016.
Putney, "Encapsulation of proteins for improved delivery," Current Opinion in Chemical Biology, Aug. 1998, vol. 2, No. 4, pp. 548-552.
Rabinovitch, Peter, "Mitochondrial Oxidative Stress and Cardiac Aging," Basic Cardiovascular Sciences, (2011), Presentation (19 pages).
Reddy, "Controlled-Release, Pegylation, Liposomal Formulations: New Mechanisms in the Delivery of Injectable Drugs," Ann Pharmacother., Jul./Aug. 2000, vol. 34, pp. 915-923.
Reddy, P. Hemachandra, "Amyloid beta Toxicity, Mitochondrial Dysfunction and Synaptic Damage in Alzheimer's Disease: Implications for Mitochondria-Targeted Antioxidant Therapeutics," New York Academy of Sciences, (2010), Abstract (1 page).
Reddy, Tejaswini P. et al., "Toxicity of Neurons Treated with Herbicides and Neuroprotection by Mitochondria-Targeted Antioxidant SS31," Int. J. Environ. Res. & Public Health, (2011), 8, pp. 203-221.
Ricciarelli, et al., "Vitamin E Reduces the Uptake of Oxidized LDL by Inhibiting CD36 Scavenger Receptor Expression in Cultured Aortic Smooth Muscle Cells", Circulation, (2000), vol. 102, pp. 82-97, American Heart Association.
Richard, et al., "Cell-penetrating Peptides," Journal of Biological Chemistry, (2003), 278(1), pp. 585-590.
Rios-Vazquez et al. "Peroxisome Proliferator-Activated Receptor-γ Agonists for Management and Prevention of Vascular Disease in Patients with and without Diabetes Mellitus," Am J Cardiovasc Drugs, vol. 6, No. 4. (2006) (pp. 231-242).
Romano, et al., "Contrast agents and renal cell apoptosis," European Heart Journal, 29:2569-2576 (2008).
Rudinger, "Characteristics of the amino acids as components of a peptide hormone sequence," Peptide Hormones, Ed. J. A. Parson, University Park Press, Baltimore, pp. 1-7, 1976.
Sabbah, Hani N. et al., "Acute Intravenous Infusion of Bendavia (MTP-131), A Novel Mitochondria-Targeting Peptide, Improves Left Ventricular Systolic Function in Dogs With Advanced Heart Failure," American Heart Association, Nov. 20, 2012, Abstract, 1 page.
Schiller et al., "Dermorphin analogues carrying an increased positive net charge in their "message" domain display extremely high μ-opioid receptor selectivity," J. Med. Chem., 32(3):698-703, 1989.
Schiller et al., "Opioid peptide analogs with novel activity profiles as potential therapeutic agents for use in analgesia," Peptide Science-Present and Future, Proc. 1st Int. Pept. Symp., 665-669, 1999.
Schiller et al., "Synthesis and in vitro opioid activity profiles of DALDA analogues," European Journal of Medicinal Chemistry, 35(10):895-901, 2000.
Schiller et al., "Tipp: A highly potent and stable pseudopeptide opioid receptor antagonist with extraordinary selectivity," J. Med. Chem., 36:3182-3187, 1993.
Schiller et al., "Unsulfated C-terminal 7-peptide of cholecystokinin: a new ligand of the opiate receptor," Biochemical and Biophysical Research Communications, 85(4):1332-1338, 1978.
Schiller, et al., "Opioid peptide analogs with novel activity profiles as potential therapeutic agents for use in analgesia," Stn Caplus, 132:102403, 1997.
Schinzel et al., "Cyclophilin D is a component of mitochondrial permeability transition and mediates neuronal cell death after focal cerebral ischemia," PNAS, 102(34), pp. 12005-12010, Aug. 23, 2005.
Schumer, et al., "Morphologic, Biochemical, and Molecular Evidence of Apoptosis During the Reperfusion Phase After Brief Periods of Renal Ischemia," American Journal of Pathology, 140(4):831-838 (1992).

(56) References Cited

OTHER PUBLICATIONS

Schwarze, et al., "In vivo protein transduction: intracellular delivery of biologically active proteins, compounds and DNA," Trends in Pharmacological Sciences, 21(2):45-48, 2000.
Search Report in EP Patent Application No. 17172250.7 dated Oct. 30, 2017.
Second Office Action in CN Patent Application No. 200680040019.2 dated Dec. 22, 2010 (English translation only) (5 pages).
Second Office Action in CN Patent Application No. 201210028972.2 dated Jan. 2, 2014 (English translation only) (6 pages).
Second Office Action in CN Patent Application No. 2013106271568 dated Sep. 2, 2015 (English translation only) (7 pages).
Sharma, Lokendra Kumar et al., "Mitochondrial respiratory complex I dysfunction promotes tumorigenesis through ROS alteration and AKT activation," Hum. Mol. Genet., (2011), vol. 20, No. 23, pp. 4605-4616.
Shimoyama, et al., "Antinociceptive and respiratory effects of intrathecal H-Tyr-D-Arg-Phe-Lys-NH2 (DALDA) and [Dmt1]DALDA," The Journal of Pharmacology and Experimental Therapeutics, 297(1):364-371, 2001.
Shroff, et al., "Effects of intrathecal opioid on extubation time, analgesia and intensive care unit stay following coronary artery bypass grafting," Journal of Clinical Anesthesia, 9:415-419, 1997.
Simmons, Zachary, "Management strategies for patients with Amyotrophic Lateral Sclerosis from diagnosis through death," The Neurologist, abstract only (File Medline on STN. An No. 2005478947), 11(5):257-270, 2005.
Skolnick et al., "From genes to protein structure and function: novel applications of computational approaches in the genomic era," Trends in Biotech, 18(1):34-39, 2000.
Sloan, Ruben C. et al., "Mitochondrial permeability transition in the diabetic heart: Contributions of thiol redox state and mitochondrial calcium to augmented reperfusion injury," J. Mol. Cell. Cardiol., (2012), 52, pp. 1009-1018.
Smith et al., "The challenges of genome sequence annotation or the devil is in the details," Nature Biotechnology, 15:1222-1223, 1997.
Song et al., "A Potent Opiate Agonist Protects Against Myocardial Stunning During Myocardial Ischemia and Reperfusion in Rats," Coronary Artery Disease, 16(6):407-410, 2005.
Spetea, et al., "Interaction of agonist peptides [3H]Tyr-D-Ala-Phe-Phe-NH2 with mu-opioid receptor in rat brain and CHO-mu/1 cell line," Peptides, 19(6):1091-1098, 1998.
Sriram et al., "Experimental allergic encephalomyelitis: A Misleading Model of Multiple Sclerosis," Ann. Neurol., 58:939-945, 2005.
Susztak, et al., "Multiple Metabolic Hits Converge on CD36 as Novel Mediator of Tubular Epithelial Apoptosis in Diabetic Nephropathy", PLOS Medicine, (2005), vol. 2, No. 2, article e45, pp. 0152-0161.
Szeto, "Development of Mitochondria-targeted Aromatic-cationic Peptides for Neurodegenerative Diseases," Ann. N.Y. Acad. Sci., (2008), 1147, pp. 112-121.
Szeto, et al., "In Vivo Disposition of Dermorphin Analog (DALDA) in Nonpregnant and Pregnant Sheep1," The Journal of Pharmacology and Experimental Therapeutics, (1998), 284(1), pp. 61-65.
Szeto, et al., "In vivo Pharmacokinetics of Selective μ-Opioid Peptide Agonists," The Journal of Pharmacology and Experimental Therapeutics, (2001), 298(1), pp. 57-61.
Szeto, et al., "Mu-opioid receptor densensitization and resensitization in vivo," International Narcotics Research Conference, Poster Abstracts, Monday, Mon19:5, 1999.
Szeto, et al., "Novel Therapies Targeting Inner Mitochondrial Membrane—from Discovery to Clinical Development", Pharm. Res., (2011), vol. 28, pp. 2669-2679.
Szeto, et al., "Respiratory depression after intravenous administration of d-selective opioid peptide analogs," Peptides, (1999), 20, pp. 101-105.
Szeto, Hazel H. "Mitochondria-targeted peptide antioxidants: Novel Neuroprotective Agents," The AAPS Journal, (2006), 8(3), Article 62, pp. E521-E531.
Szeto, Hazel H. et al., "Mitochondria-Targeted Peptide Accelerates ATP Recovery and Reduces Ischemic Kidney Injury," J. Am. Soc. Nephrol., (2011), 22, pp. 1041-1052.
Szeto, Hazel H. et al., "Mitochondria-targeting peptide (SS-31, Bendavia®) prevents microvascular rarafaction, inflammation, and fibrosis caused by ischemia-reperfusion injury," American Society of Nephrology, (2012), Abstract (1 page).
Szeto, Hazel H., "Cell-permeable, Mitochondrial-targeted, Peptide Antioxidants," The AAPS Journal, (2006), 8(2) Article 32, pp. E277-E283.
Szeto, Hazel H., "Mitochondrial Protection as Strategy to treat Ischemia-Reperfusion Injury," American Society of Nephrology, (2010), Presentation (17 pages).
Szeto, Hazel H., "The development of a therapeutic peptide for mitochondrial protection—from bench to bedside," Experimental Biology, (2011), Poster Presentation (1 page).
Szeto, Hazel H., "Mitochondria-Targeted Cytoprotective Peptides for Ischemia-Reperfusion Injury," Antioxid. Redox Signal, (2008), vol. 10, No. 3, pp. 601-619.
Szeto, Hazel H., et al., "Rapid Restoration of ATP by SS-31, an Inhibitor of Mitochondrial Permeability Transition, Prevents Tubular Cytoskeletal Rearrangement in Renal Ischemia-Reperfusion Injury," American Society of Nephrology, (2010), Poster Presentation (1 page).
Third Office Action in CN Patent Application No. 200680040019.2 dated Nov. 24, 2011 (8 pages).
Third Office Action in CN Patent Application No. 2012100289722 dated Jun. 30, 2014 (English translation only) (6 pages).
Thomas, et al., "Mitochondrial Targeting with Antioxidant Peptide SS-31 Prevents Mitochondrial Depolarization, Reduces Islet Cell Apoptosis, Increases Islet Cell Yield, and Improves Posttransplantation Function," J. Am. Soc. Nephrol. 18:213-222 (2007).
Tiganis, Tony, "Reactive Oxygen Species & NAPDH Oxidases in Insulin Signalling," NOX Gordon Research Conference, (Jun. 3-8, 2012), Presentation (44 pages).
Unger, et al., "Hyperglycaemia as an inducer as well as a consequence of impaired islet cell function and insulin resistance: implications for the management of diabetes," Diabetologia, (1985), vol. 28, No. 3, pp. 119-121.
Wang, Dantong et al., "Elevated Mitochondrial Reactive Oxygen Species Generation Affects the Immune Response via Hypoxia-Inducible Factor-1α in Long-Lived Mclk1+/- Mouse Mutants," J. Immunol., (2010), 184(2), pp. 582-590.
Wang, Tongyu, "Study progress on the relationship between oxidized low density lipoprotein and artherosclerosis," Foreign Medical Sciences (Geriatrics), 25(1):34-38, Jan. 31, 2004 (in Chinese).
Waugh et al., "Pioglitazone: A review of its use in type 2 diabetes mellitus," Drugs, vol. 66, No. 1, pp. 85-109, Feb. 2006.
Weiner, Alan L., "Liposomes for Protein Delivery: Selecting Manufacture and Development Processes," Immunomethods, Jun. 1994, vol. 4, No. 3, pp. 201-209.
Wells, "Additivity of Mutational Effects in Proteins," Biochemistry, American Chemical Society, (1990), 29(37), pp. 8509-8517.
Whiteman, Matthew et al., "Do Mitochondriotropic Antioxidants Prevent Chlorinative Stress-Induced Mitochondrial and Cellular Injury?" Antioxid. Redox Signal., (2008), vol. 10, No. 3, pp. 641-650.
Wu, et al. "A highly potent peptide analgesic that protects against ischemia-reperfusion-induced myocardial stunning", Am. J. Physiol. Heart. Circ. Physiol., Aug. 2002, vol. 283, No. 2, pp. H783-H791.
Wu, et al., "Myocardial protective effect of mu opioid agonists," International Narcotics Research Conference, Poster Abstracts, Sun59:15, 1999.
Yan, et al., "Recent advances in molecular mechanisms of cerebral ischemic injury," Chinese Journal of Pathophysiology 19(3):423-426 (2003) (in Chinese; English abstract).
Yang, Lichuan et al., "Mitochondria Targeted Peptides Protect against 1-Methyl-4-Phenyl-1,2,3,6-Tetrahydropyridine Neurotoxicity," Antioxid Redox Signal., (2009), vol. 11, No. 9, pp. 2095-2104.
Zadina, et al., "A potent and selective endogenous agonist for the mu-opiate receptor," Nature, 386:499-502, 1997.

(56) References Cited

OTHER PUBLICATIONS

Zhao, et al., "Profound spinal tolerance after repeated exposure to a highly selective u-opioid peptide agonist: Role of o-opioid receptors," J Pharma. Exper. Thera., 302(1):188-196, 2002.

Zhao, et al., "Transcellular Transport of a Highly Polar 3+ Net Charge Opioid Tetrapeptide," Journal of Pharmacology and Experimental Therapeutics, 2003, vol. 304, No. 1, pp. 425-432.

Zhao, et al., "Translocation of a 3+ net charge tetrapeptide across plasma membrane of mammalian cells," Abstract published on-line May 1, 2002, World Congress of Pharmacology Meeting, held Jul. 2002.

Zhao, Guo-Min et al., "Comparison of [Dmt1]DALDA and DAMGO in Binding and G Protein Activation at μ, δ, and κ Opioid Receptors," J. Parmacology and Experimental Therapeutics, (2003), vol. 307, No. 3, pp. 947-954.

Zhao, Kesheng et al., "Mitochondria-targeted peptide prevents mitochondrial depolarization and apoptosis induced by tert-butyl hydroperoxide in neuronal cell lines," Biochem. Pharmacol., (2005), 70, pp. 1796-1806.

Zhu et al., "Histone Deacetylase-3 Activation Promotes Tumor Necrosis Factor-α (TNF-α) Expression in Cardiomyocytes during Lipopolysaccharide Stimulation," J. Biol. Chem., Mar. 2010, vol. 285, No. 13, pp. 9429-9436.

Zhu et al., "MicroRNA-195 promotes palmitate-induced apoptosis in cardiomyocytes by down-regulating Sirtl", Cardiovasc. Res., Oct. 1, 2011, vol. 92, No. 1, pp. 75-84.

\* cited by examiner

Figure 12A Background

Figure 12C Normal heart

Figure 12E 18 h ischemic storage with St. Thomas solution alone

Figure 12G 18 h ischemic storage with 1 nM SS31 in St. Thomas solution

Figure 12I 18 h ischemic storage with 100 nM SS20 in St. Thomas solution

HNE

Normal heart 18 h cold ischemia w/ St. Thomas soln 18 h cold ischemia w/ 1 nM SS-31

18 h cold ischemia w/ 100 nM SS-20

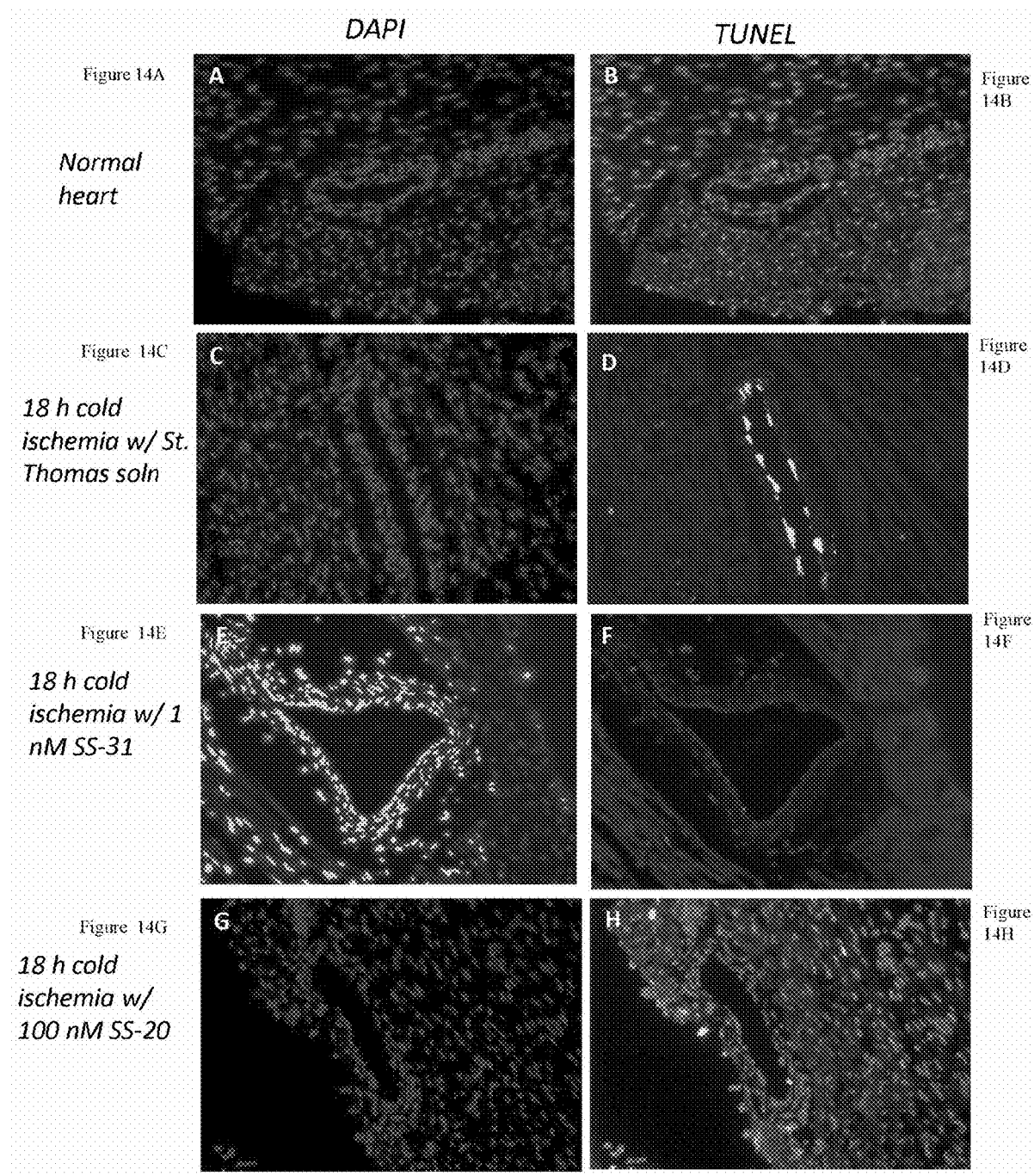

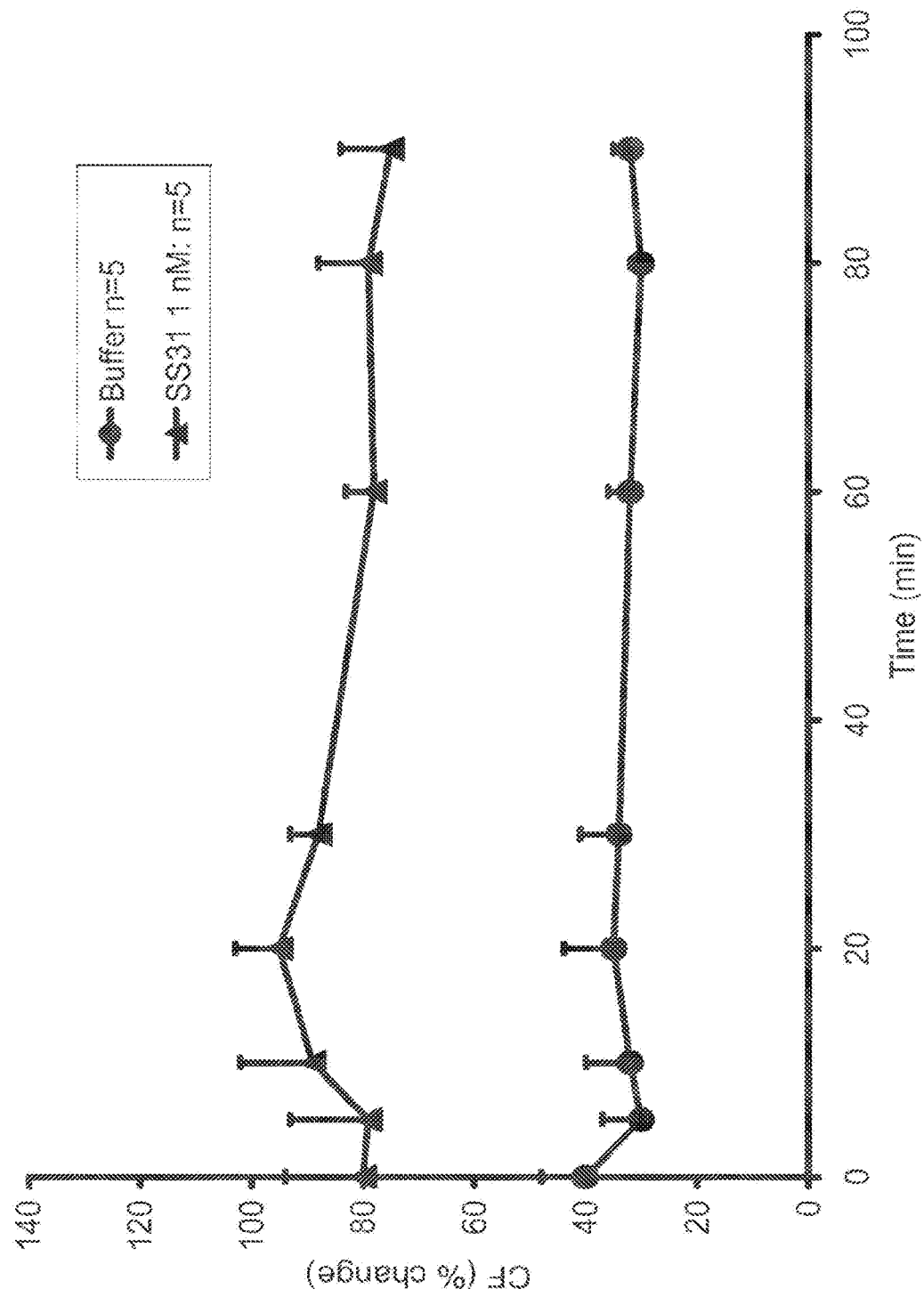

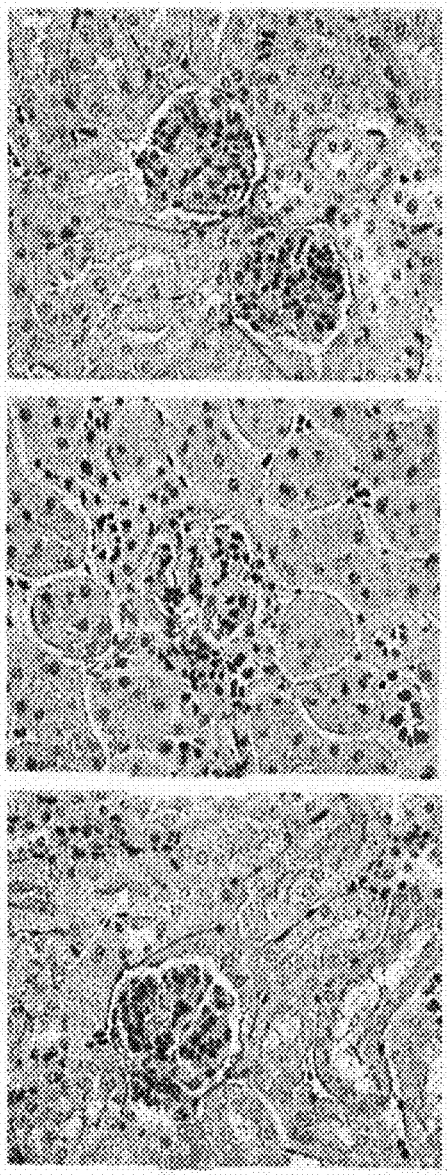

METHODS FOR REDUCING CD36 EXPRESSION

CROSS-REFERENCE TO RELATED PATENT APPLICATIONS

This application is a continuation of U.S. application Ser. No. 16/140,325, filed Sep. 24, 2018, which is a continuation of U.S. application Ser. No. 15/369,281, filed Dec. 5, 2016, which is a continuation of U.S. application Ser. No. 14/285,226, filed May 22, 2014, which is a continuation of U.S. application Ser. No. 14/075,686, filed Nov. 8, 2013, now U.S. Pat. No. 9,150,614, issued Oct. 6, 2015, which is a continuation of U.S. application Ser. No. 12/850,079, filed Aug. 4, 2010, now U.S. Pat. No. 8,603,971, issued Dec. 10, 2013, which is a continuation of U.S. application Ser. No. 12/434,216, filed May 1, 2009, now U.S. Pat. No. 7,811,987, issued Oct. 12, 2010, which is a continuation of U.S. application Ser. No. 11/532,764, filed on Sep. 18, 2006, now U.S. Pat. No. 7,541,340, issued Jun. 2, 2009, which claims priority to U.S. Provisional Application Ser. No. 60/718,170, filed on Sep. 16, 2005, the contents of which are hereby incorporated by reference in their entireties.

STATEMENT OF GOVERNMENT SUPPORT

The invention described in this application was funded by the National Institute of Drug Abuse, Grant No. P01 DA08924, the National Institute of Neurological Diseases and Stroke, Grant No. R21 NS48295, and the National Heart, Lung and Blood Institute, Grant No. RO1 HL082511. The United States Government has certain rights in this invention.

BACKGROUND OF THE INVENTION

CD36 is a transmembrane protein of the class B scavenger receptor family. The protein is widely expressed on numerous cells, such as microvascular endothelium, macrophages, platelets, adipocytes, epithelial cells (e.g., intestinal epithelial and renal tubular cells, etc.), pancreatic islet cells and cardiac muscle. The receptor may interact with multiple extracellular ligands, such as thrombospondin-1, long-chain fatty acids, and oxidized low-density lipoprotein.

Abnormal expression of CD36 has been implicated in a wide variety of diseases and conditions. For example, mice lacking CD36 have less atherosclerotic lesions when fed a Western diet compared to wild-type mice. Further, CD36 knock out mice were reported to be protected against acute cerebral ischemia.

Therefore, methods for reducing expression of CD36 expression are beneficial for treating a disease or condition characterized by abnormal expression of CD36.

SUMMARY OF THE INVENTION

In one embodiment, the invention provides a method for reducing CD36 expression in a cell. The method comprises contacting the cell with an effective amount of an aromatic-cationic peptide.

In another embodiment, the invention provides a method for reducing CD36 expression in a mammal in need thereof. The method comprises administering to the mammal an effective amount of an aromatic-cationic peptide.

In yet another embodiment, the invention provides a method for treating a disease or condition characterized by increased CD36 expression in a mammal in need thereof. The method comprises administering to the mammal an effective amount of an aromatic-cationic peptide.

In a further embodiment, the invention provides a method for treating ureteral obstruction in a mammal in need thereof. The method comprises administering to the mammal an effective amount of an aromatic-cationic peptide.

In yet a further embodiment, the invention provides a method for treating diabetic nephropathy in a mammal in need thereof. The method comprises administering to the mammal an effective amount of an aromatic-cationic peptide.

In another embodiment, the invention provides a method for reducing CD36 expression in a removed organ or tissue. The method comprises administering to the mammal an effective amount of an aromatic-cationic peptide.

The aromatic-cationic peptides useful in the methods of the present invention have at least one net positive charge; a minimum of four amino acids; a maximum of about twenty amino acids; a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1.

BRIEF DESCRIPTION OF THE FIGURES

FIGS. 12A-12J. Cold storage of isolated hearts with SS-31 or SS-20 prevented upregulation of CD36 expression. The "background" control (FIGS. 12A and 12B) represents two sections from a normal non-ischemic heart that were not treated with the primary anti-CD-36 antibody. "Normal heart" (FIGS. 12C and 12D) represents two sections obtained from a non-ischemic heart. The sections from a representative heart stored in St. Thomas solution (FIGS. 12E and 12F) for 18 hours at 4° C. showed increased CD36 staining compared to "Normal heart." CD36 staining was significantly reduced in hearts stored with either 1 nM SS-31 (FIGS. 12G and 12H) or 100 nM SS-20 (FIGS. 12I and 12J) in St. Thomas solution.

FIGS. 14A-14H. SS-31 and SS-20 abolished endothelial apoptosis in isolated guinea pig hearts subjected to warm reperfusion after prolonged cold ischemia. Hearts subjected to 18 hours of cold storage in St. Thomas solution (FIGS. 14C and 14D); non-ischemic normal hearts (FIGS. 14A and 14B). Apoptotic cells were not observed in hearts stored in SS-31 (FIGS. 14E and 14F) or SS-20 (FIGS. 14G and 14H).

FIGS. 15A-15B. SS-31 and SS-20 preserves coronary flow in isolated guinea pig hearts subjected to warm reperfusion after prolonged cold ischemia. Guinea pig hearts perfused with a cardioplegic solution (St. Thomas solution) alone or St. Thomas solution containing either 1 nM SS-31 (FIG. 15A) or 100 nM SS-20 (FIG. 15B) for 3 min. and then subjected to 18 hours of cold ischemia (4° C.).

FIGS. 16A-16C. SS-31 prevented damage to proximal tubules in diabetic mice. Diabetes was induced by streptozotocin (STZ) injection for 5 d. Kidney sections obtained after 3 weeks showed loss of brush border in STZ-treated animals (FIG. 16A, FIG. 16B) that was not seen in mice not treated with STZ (FIG. 16A). The loss of brush border was not seen in STZ-treated animal that received daily SS-31 (3 mg/kg) (FIG. 16C).

DETAILED DESCRIPTION OF THE INVENTION

Peptides

Figure 1:
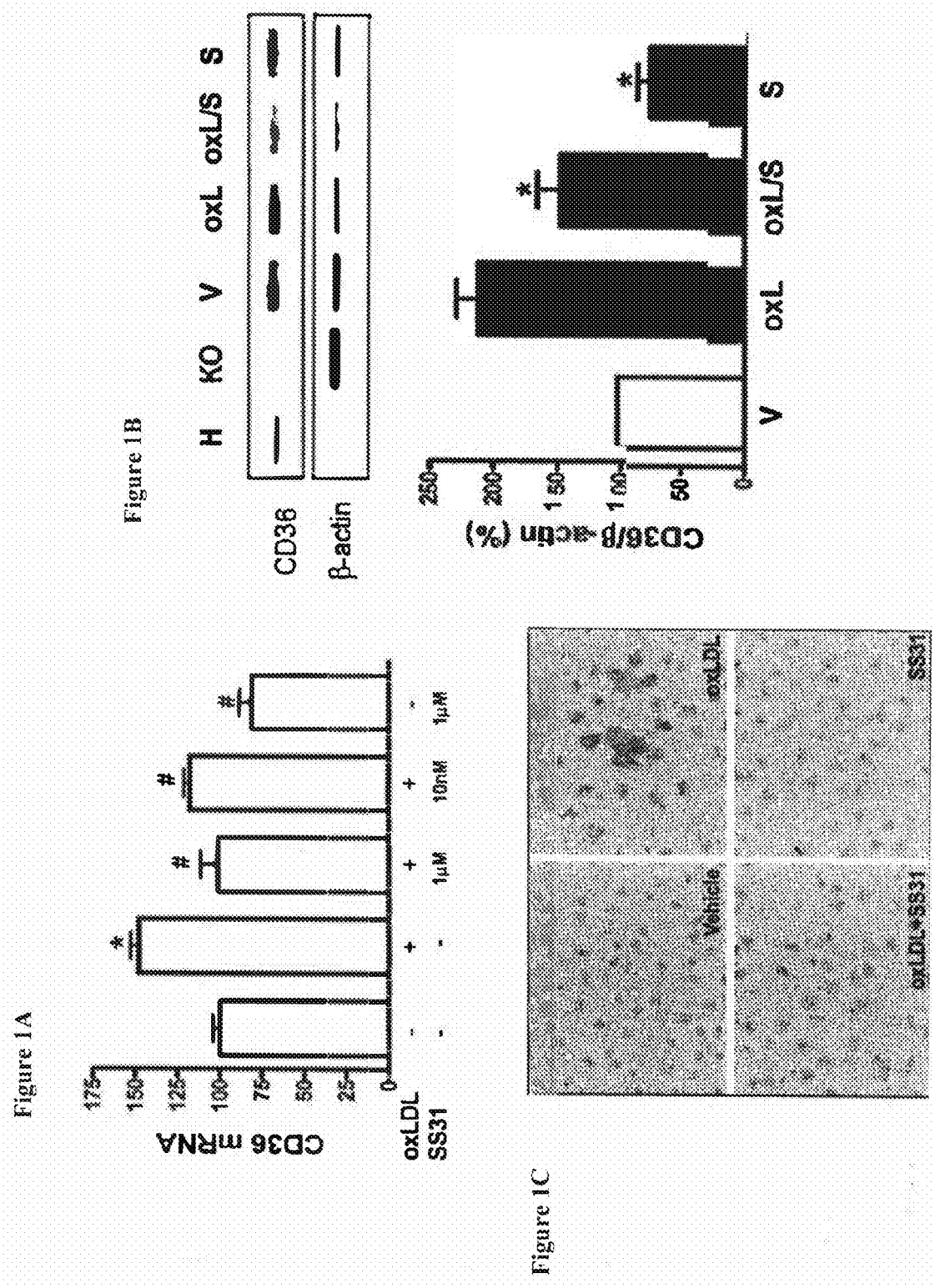
FIGS. 1A-1C. SS-31 reduced oxLDL-induced CD36 mRNA expression, CD36 protein expression, and foam cell formation in mouse peritoneal macrophages.

The invention is directed to the reduction of CD36 expression by certain aromatic-cationic peptides. The aromatic-cationic peptides are water-soluble and highly polar. Despite these properties, the peptides can readily penetrate cell membranes.

The aromatic-cationic peptides useful in the present invention include a minimum of three amino acids, and preferably include a minimum of four amino acids, covalently joined by peptide bonds.

The maximum number of amino acids present in the aromatic-cationic peptides of the present invention is about twenty amino acids covalently joined by peptide bonds. Preferably, the maximum number of amino acids is about twelve, more preferably about nine, and most preferably about six. Optimally, the number of amino acids present in the peptides is four.

The amino acids of the aromatic-cationic peptides useful in the present invention can be any amino acid. As used herein, the term "amino acid" is used to refer to any organic molecule that contains at least one amino group and at least one carboxyl group. Preferably, at least one amino group is at the position relative to a carboxyl group.

The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp) tyrosine (Tyr), and valine (Val).

Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid include hydroxyproline (Hyp).

The peptides useful in the present invention optionally contain one or more non-naturally occurring amino acids. Optimally, the peptide has no amino acids that are naturally occurring. The non-naturally occurring amino acids may be levorotary (L-), dextrorotatory (D-), or mixtures thereof.

Non-naturally occurring amino acids are those amino acids that typically are not synthesized in normal metabolic processes in living organisms, and do not naturally occur in proteins. In addition, the non-naturally occurring amino acids useful in the present invention preferably are also not recognized by common proteases.

The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid.

Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 5' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide useful in the methods of the present invention is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with for example, methyl or ethyl alcohol.

Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides useful in the methods of the invention should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids.

If the peptide contains protease sensitive sequences of amino acids, at least one of the amino acids is preferably a non-naturally occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

It is important that the aromatic-cationic peptides have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r).

The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH.

In one embodiment of the present invention, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, preferably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a).

Naturally occurring amino acids that have an aromatic group include the amino acids histidine, tryptophan, tyrosine, and phenylalanine. For example, the hexapeptide Lys-Gln-Tyr-Arg-Phe-Trp has a net positive charge of two (contributed by the lysine and arginine residues) and three aromatic groups (contributed by tyrosine, phenylalanine and tryptophan residues).

In one embodiment of the present invention, the aromatic-cationic peptides useful in the methods of the present invention have a relationship between the minimum number of aromatic groups (a) and the total number of net positive charges at physiological pH ($p_t$) wherein 3a is the largest number that is less than or equal to $p_t+1$, except that when $p_t$ is 1, a may also be 1. In this embodiment, the relationship between the minimum number of aromatic groups (a) and the total number of net positive charges ($p_t$) is as follows:

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are preferably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group.

The free carboxylate groups of the asparagine, glutamine, aspartic acid, and glutamic acid residues not occurring at the C-terminus of the aromatic-cationic peptides of the present invention may also be amidated wherever they occur within the peptide. The amidation at these internal positions may be with ammonia or any of the primary or secondary amines described above.

In one embodiment, the aromatic-cationic peptide useful in the methods of the present invention is a tripeptide having two net positive charges and at least one aromatic amino acid. In a particular embodiment, the aromatic-cationic peptide useful in the methods of the present invention is a tripeptide having two net positive charges and two aromatic amino acids.

Aromatic-cationic peptides useful in the methods of the present invention include, but are not limited to, the following peptide examples:

Lys-D-Arg-Tyr-$NH_2$,

Phe-D-Arg-His,

D-Tyr-Trp-Lys-$NH_2$,

Trp-D-Lys-Tyr-Arg-$NH_2$,

Tyr-His-D-Gly-Met,

Phe-Arg-D-His-Asp,

Tyr-D-Arg-Phe-Lys-Glu-$NH_2$,

-continued

Met-Tyr-D-Lys-Phe-Arg,

D-His-Glu-Lys-Tyr-D-Phe-Arg,

Lys-D-Gln-Tyr-Arg-D-Phe-Trp-$NH_2$,

-continued

Phe-D-Arg-Lys-Trp-Tyr-D-Arg-His,

Gly-D-Phe-Lys-Tyr-His-D-Arg-Tyr-$NH_2$,

Val-D-Lys-His-Tyr-D-Phe-Ser-Tyr-Arg-$NH_2$,

Trp-Lys-Phe-D-Asp-Arg-Tyr-D-His-Lys,

Lys-Trp-D-Tyr-Arg-Asn-Phe-Tyr-D-His-$NH_2$,

Thr-Gly-Tyr-Arg-D-His-Phe-Trp-D-His-Lys,

Asp-D-Trp-Lys-Tyr-D-His-Phe-Arg-D-Gly-Lys-$NH_2$,

D-His-Lys-Tyr-D-Phe-Glu-D-Asp-D-His-D-Lys-Arg-Trp-$NH_2$,

Ala-D-Phe-D-Arg-Tyr-Lys-D-Trp-His-D-Tyr-Gly-Phe,

Tyr-D-His-Phe-D-Arg-Asp-Lys-D-Arg-His-Trp-D-His-Phe,

Phe-Phe-D-Tyr-Arg-Glu-Asp-D-Lys-Arg-D-Arg-His-Phe-$NH_2$,

Phe-Try-Lys-D-Arg-Trp-His-D-Lys-D-Lys-Glu-Arg-D-Tyr-Thr,

Tyr-Asp-D-Lys-Tyr-Phe-D-Lys-D-Arg-Phe-Pro-D-Tyr-His-Lys,

Glu-Arg-D-Lys-Tyr-D-Val-Phe-D-His-Trp-Arg-D-Gly-Tyr-Arg-D-Met-$NH_2$,

-continued

Arg-D-Leu-D-Tyr-Phe-Lys-Glu-D-Lys-Arg-D-Trp-Lys-
D-Phe-Tyr-D-Arg-Gly,

D-Glu-Asp-Lys-D-Arg-D-His-Phe-Phe-D-Val-Tyr-Arg-
Tyr-D-Tyr-Arg-His-Phe-NH₂,

Asp-Arg-D-Phe-Cys-Phe-D-Arg-D-Lys-Tyr-Arg-D-Tyr-
Trp-D-His-Tyr-D-Phe-Lys-Phe,

His-Tyr-D-Arg-Trp-Lys-Phe-D-Asp-Ala-Arg-Cys-D-
Tyr-His-Phe-D-Lys-Tyr-His-Ser-NH₂,

Gly-Ala-Lys-Phe-D-Lys-Glu-Arg-Tyr-His-D-Arg-D-Arg-
Asp-Tyr-Trp-D-His-Trp-His-D-Lys-Asp,
and Thr-Tyr-Arg-D-Lys-Trp-Tyr-Glu-Asp-D-Lys-D-Arg-His-
Phe-D-Tyr-Gly-Val-Ile-D-His-Arg-
Tyr-Lys-NH₂.

In one embodiment, the peptides useful in the methods of the present invention have mu-opioid receptor agonist activity (i.e., they activate the mu-opioid receptor). Activation of the mu-opioid receptor typically elicits an analgesic effect.

In certain instances, an aromatic-cationic peptide having mu-opioid receptor agonist activity is preferred. For example, during short-term treatment, such as in an acute disease or condition, it may be beneficial to use an aromatic-cationic peptide that activates the mu-opioid receptor. Such acute diseases and conditions are often associated with moderate or severe pain. In these instances, the analgesic effect of the aromatic-cationic peptide may be beneficial in the treatment regimen of the human patient or other mammal. An aromatic-cationic peptide which does not activate the mu-opioid receptor, however, may also be used with or without an analgesic, according to clinical requirements.

Alternatively, in other instances, an aromatic-cationic peptide that does not have mu-opioid receptor agonist activity is preferred. For example, during long-term treatment, such as in a chronic disease state or condition, the use of an aromatic-cationic peptide that activates the mu-opioid receptor may be contraindicated. In these instances the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment.

Peptides useful in the methods of the present invention which have mu-opioid receptor agonist activity are typically those peptides which have a tyrosine residue or a tyrosine derivative at the N-terminus (i.e., the first amino acid position). Preferred derivatives of tyrosine include 2'-methyltyrosine (Mmt); 2',6'-dimethyltyrosine (2'6'Dmt); 3', 5'-dimethyltyrosine (3'5'Dmt); N,2',6'-trimethyltyrosine (Tmt); and 2'-hydroxy-6'-methyltryosine (Hmt).

In a particular preferred embodiment, a peptide that has mu-opioid receptor agonist activity has the formula Tyr-D-Arg-Phe-Lys-NH₂ (for convenience represented by the acronym: DALDA, which is referred to herein as SS-01). DALDA has a net positive charge of three, contributed by the amino acids tyrosine, arginine, and lysine and has two aromatic groups contributed by the amino acids phenylalanine and tyrosine. The tyrosine of DALDA can be a modified derivative of tyrosine such as in 2',6'-dimethyltyrosine to produce the compound having the formula 2',6'-Dmt-D-Arg-Phe-Lys-NH₂ (i.e., Dmt¹-DALDA), which is referred to herein as SS-02).

Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine.

In one embodiment, the amino acid at the N-terminus is phenylalanine or its derivative. Preferred derivatives of phenylalanine include 2-methylphenylalanine (Mmp), 2',6'-dimethylphenylalanine (Dmp), N,2',6'-trimethylphenylalanine (Tmp), and 2'-hydroxy-6'-methylphenylalanine (Hmp).

Another aromatic-cationic peptide that does not have mu-opioid receptor agonist activity has the formula Phe-D-Arg-Phe-Lys-NH₂ (i.e., Phe¹-DALDA, which is referred to herein as SS-20). Alternatively, the N-terminal phenylalanine can be a derivative of phenylalanine such as 2', 6'-dimethylphenylalanine (2'6'Dmp). DALDA containing 2',6'-dimethylphenylalanine at amino acid position 1 has the formula 2',6'-Dmp-D-Arg-Phe-Lys-NH₂, (i.e. 2'6'Dmp¹-DALDA).

In a preferred embodiment, the amino acid sequence of Dmt¹-DALDA (SS-02) is rearranged such that Dmt is not at the N-terminus. An example of such an aromatic-cationic peptide that does not have mu-opioid receptor agonist activity has the formula D-Arg-2'6'Dmt-Lys-Phe-NH₂ (referred to in this specification as SS-31).

DALDA, Phe¹-DALDA, SS-31, and their derivatives can further include functional analogs. A peptide is considered a functional analog of DALDA, Phe¹-DALDA, or SS-31 if the analog has the same function as DALDA, Phe¹-DALDA, or SS-31. The analog may, for example, be a substitution variant of DALDA, Phe¹-DALDA, or SS-31, wherein one or more amino acids are substituted by another amino acid.

Suitable substitution variants of DALDA, Phe¹-DALDA, or SS-31 include conservative amino acid substitutions. Amino acids may be grouped according to their physiochemical characteristics as follows:

(a) Non-polar amino acids: Ala(A) Ser(S) Thr(T) Pro(P) Gly(G);

(b) Acidic amino acids: Asn(N) Asp(D) Glu(E) Gln(Q);

(c) Basic amino acids: His(H4) Arg(R) Lys(K);

(d) Hydrophobic amino acids: Met(M) Leu(L) Ile(I) Val (V); and (e) Aromatic amino acids: Phe(F) Tyr(Y) Trp(W) His (H).

Substitutions of an amino acid in a peptide by another amino acid in the same group is referred to as a conservative substitution and may preserve the physiological characteristics of the original peptide. In contrast, substitutions of an amino acid in a peptide by another amino acid in a different group is generally more likely to alter the characteristics of the original peptide.

Examples of analogs useful in the practice of the present invention that activate mu-opioid receptors include, but are not limited, to the aromatic-cationic peptides shown in Table 1.

TABLE 1

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Tyr | D-Arg | Phe | Lys | | $NH_2$ |
| Tyr | D-Arg | Phe | Orn | | $NH_2$ |
| Tyr | D-Arg | Phe | Dab | | $NH_2$ |
| Tyr | D-Arg | Phe | Dap | | $NH_2$ |
| 2'6'Dmt | D-Arg | Phe | Lys | | $NH_2$ |
| 2'6'Dmt | D-Arg | Phe | Lys | Cys | $NH_2$ |
| 2'6'Dmt | D-Arg | Phe | Lys-NH(CH$_2$)$_2$—NH-dns | | $NH_2$ |
| 2'6'Dmt | D-Arg | Phe | Lys-NH(CH$_2$)$_2$—NH-atn | | $NH_2$ |
| 2'6'Dmt | D-Arg | Phe | dnsLys | | $NH_2$ |
| 2'6'Dmt | D-Cit | Phe | Lys | | $NH_2$ |
| 2'6'Dmt | D-Cit | Phe | Ahp | | $NH_2$ |
| 2'6'Dmt | D-Arg | Phe | Orn | | $NH_2$ |
| 2'6'Dmt | D-Arg | Phe | Dab | | $NH_2$ |
| 2'6'Dmt | D-Arg | Phe | Dap | | $NH_2$ |
| 2'6'Dmt | D-Arg | Phe | Ahp (2-aminoheptanoic acid) | | $NH_2$ |
| Bio-2'6'Dmt | D-Arg | Phe | Lys | | $NH_2$ |
| 3'5'Dmt | D-Arg | Phe | Lys | | $NH_2$ |
| 3'5'Dmt | D-Arg | Phe | Orn | | $NH_2$ |
| 3'5'Dmt | D-Arg | Phe | Dab | | $NH_2$ |
| 3'5'Dmt | D-Arg | Phe | Dap | | $NH_2$ |
| Tyr | D-Arg | Tyr | Lys | | $NH_2$ |
| Tyr | D-Arg | Tyr | Orn | | $NH_2$ |
| Tyr | D-Arg | Tyr | Dab | | $NH_2$ |
| Tyr | D-Arg | Tyr | Dap | | $NH_2$ |
| 2'6'Dmt | D-Arg | Tyr | Lys | | $NH_2$ |
| 2'6'Dmt | D-Arg | Tyr | Orn | | $NH_2$ |
| 2'6'Dmt | D-Arg | Tyr | Dab | | $NH_2$ |
| 2'6'Dmt | D-Arg | Tyr | Dap | | $NH_2$ |
| 2'6'Dmt | D-Arg | 2'6'Dmt | Lys | | $NH_2$ |
| 2'6'Dmt | D-Arg | 2'6'Dmt | Orn | | $NH_2$ |
| 2'6'Dmt | D-Arg | 2'6'Dmt | Dab | | $NH_2$ |
| 2'6'Dmt | D-Arg | 2'6'Dmt | Dap | | $NH_2$ |
| 3'5'Dmt | D-Arg | 3'5'Dmt | Arg | | $NH_2$ |
| 3'5'Dmt | D-Arg | 3'5'Dmt | Lys | | $NH_2$ |
| 3'5'Dmt | D-Arg | 3'5'Dmt | Orn | | $NH_2$ |
| 3'5'Dmt | D-Arg | 3'5'Dmt | Dab | | $NH_2$ |
| Tyr | D-Lys | Phe | Dap | | $NH_2$ |
| Tyr | D-Lys | Phe | Arg | | $NH_2$ |
| Tyr | D-Lys | Phe | Lys | | $NH_2$ |
| Tyr | D-Lys | Phe | Orn | | $NH_2$ |
| 2'6'Dmt | D-Lys | Phe | Dab | | $NH_2$ |
| 2'6'Dmt | D-Lys | Phe | Dap | | $NH_2$ |
| 2'6'Dmt | D-Lys | Phe | Arg | | $NH_2$ |
| 2'6'Dmt | D-Lys | Phe | Lys | | $NH_2$ |
| 3'5'Dmt | D-Lys | Phe | Orn | | $NH_2$ |
| 3'5'Dmt | D-Lys | Phe | Dab | | $NH_2$ |
| 3'5'Dmt | D-Lys | Phe | Dap | | $NH_2$ |
| 3'5'Dmt | D-Lys | Phe | Arg | | $NH_2$ |
| Tyr | D-Lys | Tyr | Lys | | $NH_2$ |
| Tyr | D-Lys | Tyr | Orn | | $NH_2$ |
| Tyr | D-Lys | Tyr | Dab | | $NH_2$ |
| Tyr | D-Lys | Tyr | Dap | | $NH_2$ |
| 2'6'Dmt | D-Lys | Tyr | Lys | | $NH_2$ |
| 2'6'Dmt | D-Lys | Tyr | Orn | | $NH_2$ |
| 2'6'Dmt | D-Lys | Tyr | Dab | | $NH_2$ |
| 2'6'Dmt | D-Lys | Tyr | Dap | | $NH_2$ |
| 2'6'Dmt | D-Lys | 2'6'Dmt | Lys | | $NH_2$ |
| 2'6'Dmt | D-Lys | 2'6'Dmt | Orn | | $NH_2$ |
| 2'6'Dmt | D-Lys | 2'6'Dmt | Dab | | $NH_2$ |
| 2'6'Dmt | D-Lys | 2'6'Dmt | Dap | | $NH_2$ |
| 2'6'Dmt | D-Arg | Phe | dnsDap | | $NH_2$ |
| 2'6'Dmt | D-Arg | Phe | atnDap | | $NH_2$ |
| 3'5'Dmt | D-Lys | 3'5'Dmt | Lys | | $NH_2$ |
| 3'5'Dmt | D-Lys | 3'5'Dmt | Orn | | $NH_2$ |
| 3'5'Dmt | D-Lys | 3'5'Dmt | Dab | | $NH_2$ |
| 3'5'Dmt | D-Lys | 3'5'Dmt | Dap | | $NH_2$ |
| Tyr | D-Lys | Phe | Arg | | $NH_2$ |
| Tyr | D-Orn | Phe | Arg | | $NH_2$ |
| Tyr | D-Dab | Phe | Arg | | $NH_2$ |
| Tyr | D-Dap | Phe | Arg | | $NH_2$ |
| 2'6'Dmt | D-Arg | Phe | Arg | | $NH_2$ |
| 2'6'Dmt | D-Lys | Phe | Arg | | $NH_2$ |
| 2'6'Dmt | D-Orn | Phe | Arg | | $NH_2$ |
| 2'6'Dmt | D-Dab | Phe | Arg | | $NH_2$ |
| 3'5'Dmt | D-Dap | Phe | Arg | | $NH_2$ |
| 3'5'Dmt | D-Arg | Phe | Arg | | $NH_2$ |
| 3'5'Dmt | D-Lys | Phe | Arg | | $NH_2$ |
| 3'5'Dmt | D-Orn | Phe | Arg | | $NH_2$ |
| Tyr | D-Lys | Tyr | Arg | | $NH_2$ |
| Tyr | D-Orn | Tyr | Arg | | $NH_2$ |
| Tyr | D-Dab | Tyr | Arg | | $NH_2$ |
| Tyr | D-Dap | Tyr | Arg | | $NH_2$ |
| 2'6'Dmt | D-Arg | 2'6'Dmt | Arg | | $NH_2$ |
| 2'6'Dmt | D-Lys | 2'6'Dmt | Arg | | $NH_2$ |
| 2'6'Dmt | D-Orn | 2'6'Dmt | Arg | | $NH_2$ |
| 2'6'Dmt | D-Dab | 2'6'Dmt | Arg | | $NH_2$ |
| 3'5'Dmt | D-Dap | 3'5'Dmt | Arg | | $NH_2$ |
| 3'5'Dmt | D-Arg | 3'5'Dmt | Arg | | $NH_2$ |
| 3'5'Dmt | D-Lys | 3'5'Dmt | Arg | | $NH_2$ |
| 3'5'Dmt | D-Orn | 3'5'Dmt | Arg | | $NH_2$ |
| Mmt | D-Arg | Phe | Lys | | $NH_2$ |
| Mmt | D-Arg | Phe | Orn | | $NH_2$ |
| Mmt | D-Arg | Phe | Dab | | $NH_2$ |
| Mmt | D-Arg | Phe | Dap | | $NH_2$ |
| Tmt | D-Arg | Phe | Lys | | $NH_2$ |
| Tmt | D-Arg | Phe | Orn | | $NH_2$ |
| Tmt | D-Arg | Phe | Dab | | $NH_2$ |
| Tmt | D-Arg | Phe | Dap | | $NH_2$ |
| Hmt | D-Arg | Phe | Lys | | $NH_2$ |
| Hmt | D-Arg | Phe | Orn | | $NH_2$ |
| Hmt | D-Arg | Phe | Dab | | $NH_2$ |
| Hmt | D-Arg | Phe | Dap | | $NH_2$ |
| Mmt | D-Lys | Phe | Lys | | $NH_2$ |
| Mmt | D-Lys | Phe | Orn | | $NH_2$ |
| Mmt | D-Lys | Phe | Dab | | $NH_2$ |
| Mmt | D-Lys | Phe | Dap | | $NH_2$ |
| Mmt | D-Lys | Phe | Arg | | $NH_2$ |
| Tmt | D-Lys | Phe | Lys | | $NH_2$ |
| Tmt | D-Lys | Phe | Orn | | $NH_2$ |
| Tmt | D-Lys | Phe | Dab | | $NH_2$ |
| Tmt | D-Lys | Phe | Dap | | $NH_2$ |
| Tmt | D-Lys | Phe | Arg | | $NH_2$ |
| Hmt | D-Lys | Phe | Lys | | $NH_2$ |
| Hmt | D-Lys | Phe | Orn | | $NH_2$ |
| Hmt | D-Lys | Phe | Dab | | $NH_2$ |
| Hmt | D-Lys | Phe | Dap | | $NH_2$ |
| Hmt | D-Lys | Phe | Arg | | $NH_2$ |
| Mmt | D-Lys | Phe | Arg | | $NH_2$ |
| Mmt | D-Orn | Phe | Arg | | $NH_2$ |
| Mmt | D-Dab | Phe | Arg | | $NH_2$ |
| Mmt | D-Dap | Phe | Arg | | $NH_2$ |
| Mmt | D-Arg | Phe | Arg | | $NH_2$ |
| Tmt | D-Lys | Phe | Arg | | $NH_2$ |
| Tmt | D-Orn | Phe | Arg | | $NH_2$ |
| Tmt | D-Dab | Phe | Arg | | $NH_2$ |
| Tmt | D-Dap | Phe | Arg | | $NH_2$ |
| Tmt | D-Arg | Phe | Arg | | $NH_2$ |
| Hmt | D-Lys | Phe | Arg | | $NH_2$ |
| Hmt | D-Orn | Phe | Arg | | $NH_2$ |
| Hmt | D-Dab | Phe | Arg | | $NH_2$ |

TABLE 1-continued

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Hmt | D-Dap | Phe | Arg | | $NH_2$ |
| Hmt | D-Arg | Phe | Arg | | $NH_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of analogs useful in the practice of the present invention that do not activate mu-opioid receptors include, but are not limited to, the aromatic-cationic peptides shown in Table 2.

TABLE 2

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |

Cha = cyclohexyl

The amino acids of the peptides shown in table 1 and 2 may be in either the L- or the D-configuration.

Methods

The aromatic-cationic peptides described above are useful in reducing CD36 expression in a cell. For the purposes of this specification CD36 expression in a cell is considered to be reduced if the expression of CD36 is decreased by about 10%, preferably by about 25%, more preferably by about 50%, even more preferably by about 75%. Optimally, CD36 is reduced to about normal levels in a cell.

CD36 is expressed on a wide variety of cells. Examples of such cells include macrophages, platelets, adipocytes, endothelial cells such as microvascular endothelial cells and umbilical vein endothelial cells; epithelial cells such as intestinal epithelial cells, gall bladder epithelial cells, bladder epithelial cells, bronchial epithelial cells and alveolar epithelial cells; renal tubular cells; pancreatic islet cells; hepatocytes; skeletal muscle cells; cardiac muscle cells; neuronal cells; glia cells; pancreas cells; sperm cells; etc.

For the purposes of this specification, cells expressing about 10%, typically about 25%, about typically about 50%, and even more typically about 75% more CD36 than normal cells are considered to express increased levels of CD36.

In one embodiment, the invention provides a method for reducing CD36 expression in a cell. Any cell that expresses CD36 can be used in the method of the invention, and include those mentioned above. The method for reducing CD36 expression in a cell comprises contacting the cell with an effective amount of an aromatic-cationic peptide described above.

In another embodiment, the invention provides a method for reducing CD36 expression in a mammal in need thereof. The method for reducing CD36 expression in the mammal comprises administering to the mammal an effective amount of an aromatic-cationic peptide described herein.

Mammals in need of reducing CD36 expression include, for example, mammals that have increased CD36 expression. The increased expression of CD36 is associated with various diseases and conditions. Examples of diseases and conditions characterized by increased CD36 expression include, but are not limited to, atherosclerosis, inflammation, abnormal angiogenesis, abnormal lipid metabolism, abnormal removal of apoptotic cells, ischemia such as cerebral ischemia and myocardial ischemia, ischemia reperfusion, ureteral obstruction, stroke, Alzheimer's Disease, diabetes, diabetic nephropathy and obesity. A discussion on the involvement of CD36 in atherosclerosis may be found in "Targeted disruption of the class B scavenger receptor CD36 protects against atherosclerotic lesion development in mice," Febbraio M, Podrez E A, Smith J D, Hajjar D P, Hazen S L et al., *J Clinical Investigation,* 105:1049-1056, 2000, and "CD36: a class B scavenger receptor involved in angiogenesis, atherosclerosis, inflammation, and lipid metabolism," Febbraio M., Hajjar D P and Silverstein R L, *Journal of Clinical Investigation,* 108:785-791, 2001.

Mammals in need of reducing CD36 expression also include mammals suffering from complications of diabetes. Some complications of diabetes include, in addition to nephropathy, neuropathy, retinopathy, coronary artery disease, and peripheral vascular disease associated with diabetes.

In another embodiment, the invention relates to a method for reducing CD36 expression in removed organs and tissues. The method comprises contacting the removed organ or tissue with an effective amount of an aromatic-cationic peptide described above. An organ or tissue may, for example, be removed from a donor for autologous or heterologous transplantation. Some examples of organs and tissues include heart, lungs, pancreas, kidney, liver, skin, etc.

Synthesis of the Peptides

The peptides useful in the methods of the present invention may be synthesized by any of the methods well known in the art. Suitable methods for chemically synthesizing the protein include, for example those described by Stuart and Young in "Solid Phase Peptide Synthesis," Second Edition, Pierce Chemical Company (1984), and in "Solid Phase Peptide Synthesis," *Methods Enzymol.,* 289, Academic Press, Inc, New York (1997).

Modes of Administration

Any method known to those in the art for contacting a cell, organ or tissue with a peptide may be employed. Suitable methods include in vitro, ex vivo, or in vivo methods.

In vitro methods typically include cultured samples. For example, a cell can be placed in a reservoir (e.g., tissue culture plate), and incubated with an aromatic-cationic peptide under appropriate conditions suitable for reducing CD36 expression. Suitable incubation conditions can be readily determined by those skilled in the art.

Ex vivo methods typically include cells, organs or tissues removed from a mammal, such as a human. The cells, organs or tissues can, for example, be incubated with the peptide under appropriate conditions. The contacted cells, organs or tissues are normally returned to the donor, placed in a recipient, or stored for future use. Thus, the peptide is generally in a pharmaceutically acceptable carrier.

In vivo methods are typically limited to the administration of an aromatic-cationic peptide, such as those described above, to a mammal, preferably a human. The peptides useful in the methods of the present invention are administered to a mammal in an amount effective in reducing expression CD36 or treating the mammal. The effective amount is determined during pre-clinical trials and clinical trials by methods familiar to physicians and clinicians.

An effective amount of a peptide useful in the methods of the present invention, preferably in a pharmaceutical composition, may be administered to a mammal in need thereof by any of a number of well-known methods for administering pharmaceutical compounds. The peptide may be administered systemically or locally.

In one embodiment, the peptide is administered intravenously. For example, the aromatic-cationic peptides useful in the methods of the present invention may be administered via rapid intravenous bolus injection. Preferably, however, the peptide is administered as a constant rate intravenous infusion.

The peptide may also be administered orally, topically, intranasally, intramuscularly, subcutaneously, or transdermally. In a preferred embodiment, transdermal administration of the aromatic-cationic peptides by methods of the present invention is by iontophoresis, in which the charged peptide is delivered across the skin by an electric current.

Other routes of administration include intracerebroventricularly or intrathecally. Intracerebroventiculatly refers to administration into the ventricular system of the brain. Intrathecally refers to administration into the space under the arachnoid membrane of the spinal cord. Thus intracerebroventricular or intrathecal administration may be preferred for those diseases and conditions which affect the organs or tissues of the central nervous system.

The peptides useful in the methods of the invention may also be administered to mammals by sustained release, as is known in the art. Sustained release administration is a method of drug delivery to achieve a certain level of the drug over a particular period of time. The level typically is measured by serum or plasma concentration.

A description of methods for delivering a compound by controlled release can be found in international PCT Application No. WO 02/083106. The PCT application is incorporated herein by reference in its entirety.

Any formulation known in the art of pharmacy is suitable for administration of the aromatic-cationic peptides useful in the methods of the present invention. For oral administration, liquid or solid formulations may be used. Some examples of formulations include tablets, gelatin capsules, pills, troches, elixirs, suspensions, syrups, wafers, chewing gum and the like. The peptides can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the aromatic-cationic peptides useful in the methods of the present inventions may utilize conventional diluents, carriers, or excipients etc., such as those known in the art to deliver the peptides. For example, the formulations may comprise one or more of the following: a stabilizer, a surfactant, preferably a nonionic surfactant, and optionally a salt and/or a buffering agent. The peptide may be delivered in the form of an aqueous solution, or in a lyophilized form.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the peptide.

The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a human or an animal. Preferably the salt or buffering agent is present at a roughly isotonic concentration of about 150 mM to about 300 mM.

The formulations of the peptides useful in the methods of the present invention may additionally contain one or more conventional additive. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The mammal treated in accordance with the invention can be any mammal, including, for example, farm animals, such as sheep, pigs, cows, and horses; pet animals such as dogs and cats; laboratory animals, such as rats, mice and rabbits. In a preferred embodiment, the mammal is a human.

EXAMPLES

Example 1: SS-31 Reduced Oxidized Low-Density Lipoprotein (oxLDL)-Induced CD36 Expression and Foam Cell Formation in Mouse Peritoneal Macrophages Atherosclerosis is thought to develop as a result of lipid uptake by vascular-wall macrophages leading to the development of foam cells and the elaboration of cytokines and chemokines resulting in smooth muscle-cell proliferation. CD36 is a scavenger receptor that mediates uptake of oxLDL into macrophages and subsequent foam-cell development. CD36 knock out mice showed reduced uptake of oxLDL and reduced atherosclerosis.

CD36 expression is regulated at the transcriptional level by various cellular stimuli, including glucose and oxLDL. Macrophages were harvested from mice peritoneal cavity and culture overnight in the absence or presence of oxLDL (50 µg/ml) for 48 h. Incubation with oxLDL significantly increased CD36 mRNA (FIG. 1A). Inclusion of SS-31 (10 nM or 1 µM) to the culture medium abolished the up-regulation of CD36 (FIG. 1A). SS-31 by itself had no effect on CD36 expression.

Expression of CD36 protein, as determined by western blot, was also significantly increased after 48 h incubation with 25 µg/ml of oxLDL (oxL) when compared to vehicle control (V) (FIG. 1B). Other controls included CD36 expression from mouse heart (H) and macrophages obtained from CD36 knockout mice (KO). The amount of CD36 protein was normalized to β-actin. Incubation with SS-31 (1 µM) (S) significantly reduced CD36 protein expression compared to macrophages exposed to vehicle control (V) ($P<0.01$, ANOVA with posthoc Neuman Keuls test). Concurrent incubation with SS-31 (1 µM) also significantly inhibited the upregulation of CD36 protein expression in macrophages exposed to 25 µg/ml oxLDL for 48 h (oxL/S) ($P<0.01$, ANOVA with posthoc Neuman Keuls test).

Incubation of macrophages with oxLDL for 48 h also increased foam cell formation (FIG. 1C). Foam cell is indicated by oil red O which stains lipid droplets red. Inclusion of SS-31 (1 µM) prevented oxLDL-induced foam cell formation (FIG. 1C).

Incubation of macrophages with oxLDL increased apoptotic cells from 6.7% to 32.8%. Concurrent treatment with SS-31 (1 nM) significantly reduced the percentage of apoptotic cells induced by oxLDL to 20.8%.

Example 2: SS-31 Protected Mice from Acute Cerebral Ischemia

Cerebral ischemia initiates a cascade of cellular and molecular events that lead to brain damage. One such event is postischemic inflammation. Using a mouse model of cerebral ischemia-reperfusion (20 min. occlusion of the middle cerebral artery), it was found that CD36 was upregulated in microglia and macrophages in the post-ischemic brain, and there was increased reactive oxygen species production. CD36 knock out mice had a profound reduction in reactive oxygen species after ischemia and improved neurological function compared to wild type mice.

Cerebral ischemia was induced by occlusion of the right middle cerebral artery for 30 min. Wild-type (WT) mice were given either saline vehicle (Veh) (ip, n=19) or SS-31 (2 mg/kg or 5 mg/kg, ip, n=6) at 0, 6, 24 and 48 h after ischemia. Mice were killed 3 days after ischemia. Brains were removed, frozen, and sectioned. Brain sections were stained by the Nissl stain. Infarct volume and hemispheric swelling was determined using an image analyzer. Data were analyzed by one-way ANOVA with posthoc analysis.

Figure 2:
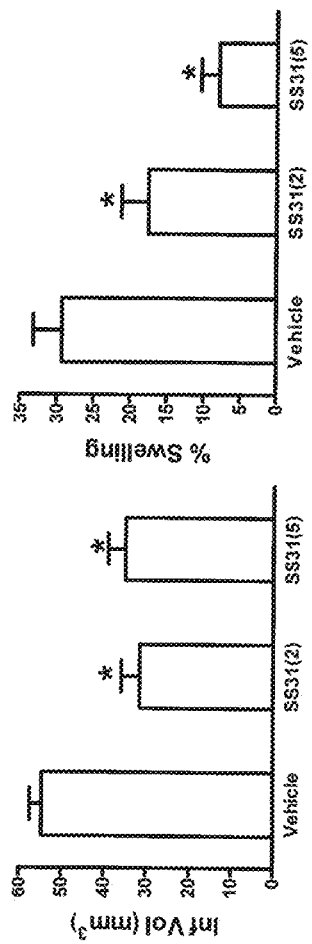
FIGS. 2A-2B. SS-31 treatment reduced infarct volume and hemispheric swelling in wild-type mice subjected to acute cerebral ischemia.

Treatment of wild type mice with SS-31 (2 mg/kg or 5 mg/kg, ip, n=6) at 0, 6, 24 and 48 hours after 30 min. occlusion of the middle cerebral artery resulted in a significant reduction in infarct volume (FIG. 2A) and hemispheric swelling (FIG. 2B) compared to saline controls. (*$P<0.05$ compared to Veh).

Figure 3:
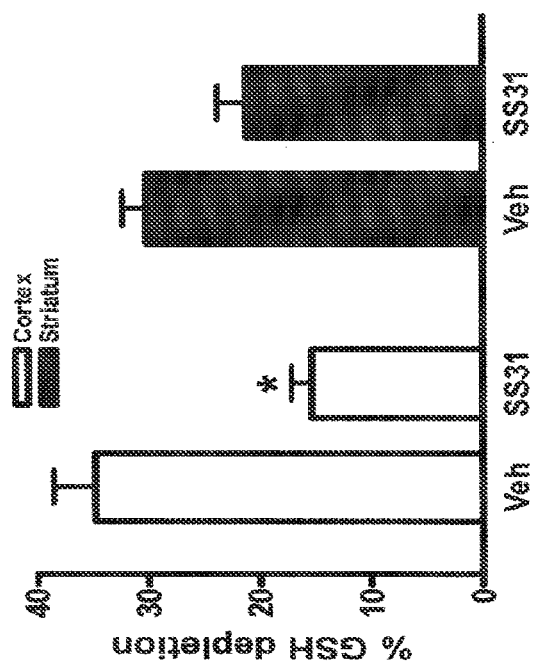
FIG. 3. SS-31 treatment reduced the decrease in reduced glutathione (GSH) in post-ischemic brain in wild-type mice.

Thirty min. cerebral ischemia in WT mice resulted in significant depletion in reduced glutathione (GSH) in the ipsilateral cortex and striatum compared to the contralateral side in vehicle-treated animals (FIG. 3). The depletion of GSH in the ipsilateral cortex was significantly reduced in mice treated with SS-31 (2 mg/kg ip at 0, 6, 24 and 48 h) (FIG. 3). The depletion of GSH in the striatum was also reduced by SS-31 treatment but did not reach statistical significance.

Figure 4:
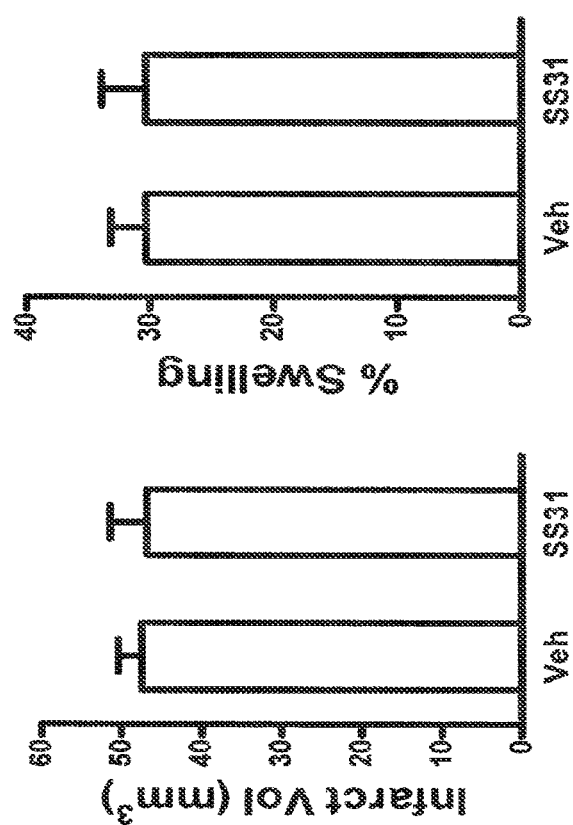
FIG. 4. SS-31 had no effect in reducing infarct volume or hemispheric swelling in CD36 knock-out mice subjected to acute cerebral ischemia.

Example 3: SS-31 Mediated Protection Against Acute Cerebral Ischemia Mimics Protection Observed in CD36 Knockout Mice CD36 knockout (CD36 KO) mice were subjected to acute cerebral ischemia as described under Example 2. CD36 KO mice were given either saline vehicle (Veh) (ip, n=5) or SS-31 (2 mg/kg, i.p. n=5) at 0, 6, 24 and 48 h after 30 min ischemia. Infarct volume (FIG. 4A) and hemispheric swelling (FIG. 4B) in CD36 KO mice were similar whether they received saline or SS-31.

Figure 5:
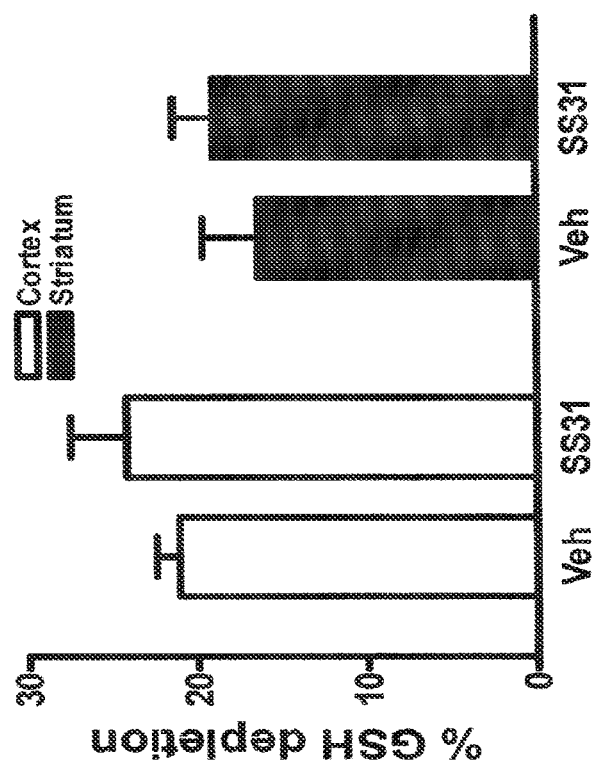
FIG. 5. SS-31 did not reduce GSH depletion in post-ischemic brain from CD36 knock-out mice.

Treatment of CD36 KO mice with SS-31 (2 mg/kg, i.p., n=5) also failed to further prevent GSH depletion in the ipsilateral cortex caused by 30 min ischemia (FIG. 5).

These data suggest that the protective action of SS-31 against acute cerebral ischemia may be mediated by inhibiting the upregulation of CD36.

Example 4: SS-31 Reduced CD36 mRNA Expression in Post-Ischemic Brain

Figure 6:
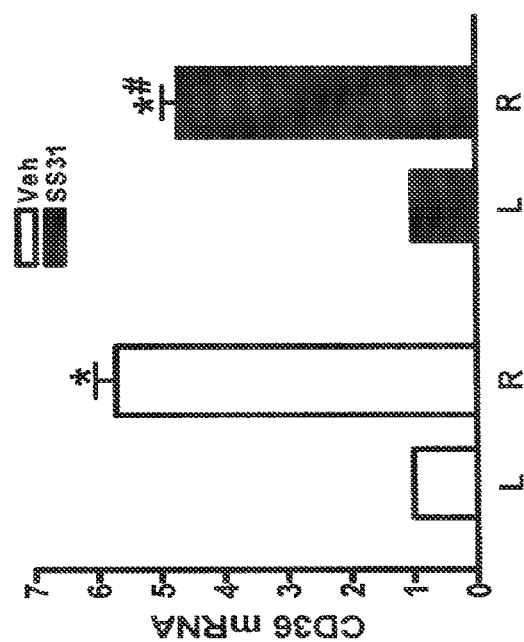
FIG. 6. SS-31 reduced CD36 mRNA expression in post-ischemic brain in wild-type mice.

Transient occlusion of the middle cerebral artery has been shown to significantly increase the expression of CD36 mRNA in microglia and macrophages in the post-ischemic brain. Wild-type mice were given saline vehicle (Veh, i.p., n=6) or SS-31 (5 mg/kg, i.p., n=6) at 0 and 6 h after 30 min ischemia, and CD36 mRNA levels were determined using real time PCR. CD36 expression was upregulated almost 6-fold in the ipsilateral brain compared to the contralateral brain in mice that received saline (FIG. 6). CD36 mRNA was significantly reduced in the ipsilateral brain in mice that received SS-31 treatment (FIG. 6).

Example 5: SS-31 Suppressed Upregulation of CD-36 in Renal Tubular Cells Following Unilateral Ureteral Obstruction Unilateral ureteral obstruction (UUO) is a common clinical disorder associated with tubular cell apoptosis, macrophage infiltration, and interstitial fibrosis. Interstitial fibrosis leads to a hypoxic environment and contributes to progressive decline in renal function despite surgical correction. CD36 has been shown to be expressed on renal tubular cells.

CD36 was found to have been upregulated in tubular cells after UUO. UUO was performed in Sprague-Dawley rats. The rats were treated with saline (ip, n=6) or SS-31 (1 mg/kg ip, n=6) one day prior to induction of UUO, and once a day for 14 days after UUO. Rats were killed, kidneys removed, embedded in paraffin and sectioned. The slides were treated with the anti-CD36 polyclonal IgG (Santa Cruz #sc-9154; 1:100 with blocking serum) at room temperature for 1.5 hours. The slides were then incubated with the second antibody conjugated with biotin (anti-rabbit IgG-G1; ABC kit, PK-6101) at room temperature for 30 min. The slides were then treated with avidin, developed with DAB and counterstained with 10% hematoxylin. The contralateral unobstructed kidney served as the control for each animal.

Figures 7A, 7B, 7C:
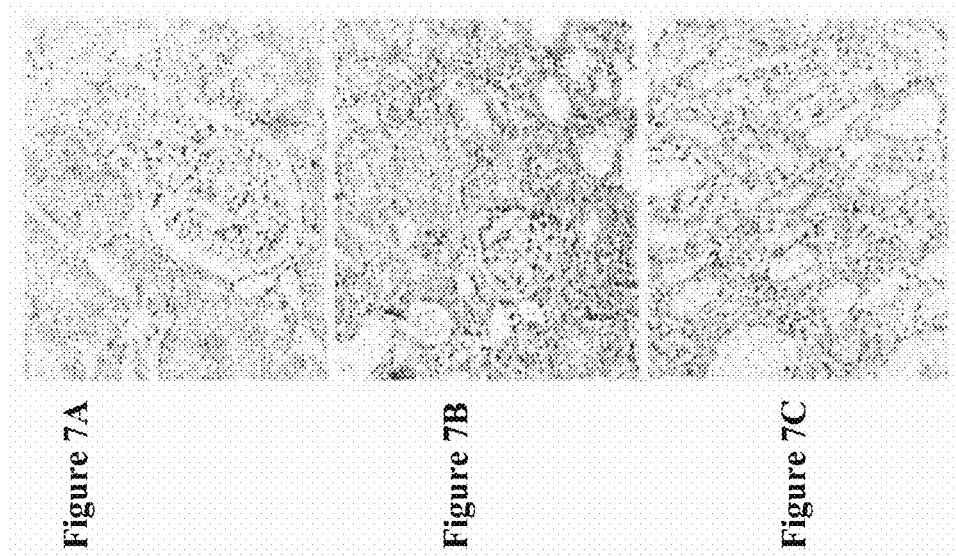
FIGS. 7A-7C. SS-31 decreases CD36 expression on renal tubular cells after unilateral ureteral obstruction (UUO). Contralateral unobstructed kidney (FIG. 7A); obstructed kidney in animals treated with saline (FIG. 7B); and obstructed kidneys obtained from rats treated with SS-31 (FIG. 7C).

UUO resulted in tubular dilation and significant increase in expression of CD36 on the tubular cells (FIG. 7). Tubular dilation was also observed in rats treated with SS-31, but there was a significant reduction in CD36 expression (FIG. 3). CD36 expression (brown stain) is primarily found on tubular cells in the contralateral unobstructed kidney (FIG. 7A). CD36 expression was increased in the obstructed kidney in animals treated with saline (FIG. 7B), but was much reduced in obstructed kidneys obtained from rats treated with SS-31 (FIG. 7C).

Figures 8A, 8B, 8C:
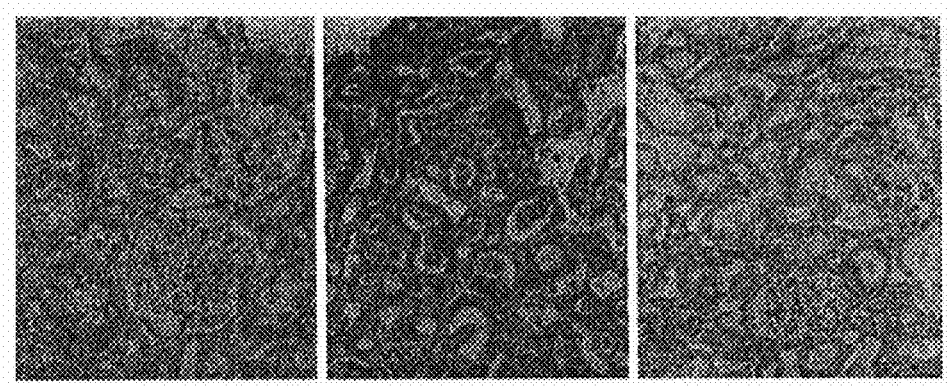
FIGS. 8A-8C. SS-31 reduces lipid peroxidation in kidney after UUO. Tubular cells in the obstructed kidney (FIG. 8B), contralateral unobstructed control (FIG. 8A); obstructed kidneys from rats treated with SS-31 (FIG. 8C).

To determine whether SS-31 reduces lipid peroxidation in kidney after UUO, rats were treated with either saline (n=6) or SS-31 (1 mg/kg ip, n=6) one day prior to induction of UUO, and once a day for 14 days UUO. Rats were then killed, kidneys removed, embedded in paraffin and sectioned. Slides were incubated with anti-HNE rabbit IgG and a biotin-linked anti-rabbit IgG was used as secondary antibody. The slides were developed with DAB. Lipid peroxidation, which was increased by UUO, was reduced by SS-31 treatment (FIG. 8). HNE stain (brown) was significantly increased in tubular cells in the obstructed kidney (FIG. 8B) compared to the contralateral control (FIG. 8A). Obstructed kidneys from rats treated with SS-31 showed significantly less HNE stain (FIG. 8C) compared to saline-treated rats (FIG. 8B).

Figures 9A, 9B, 9C:
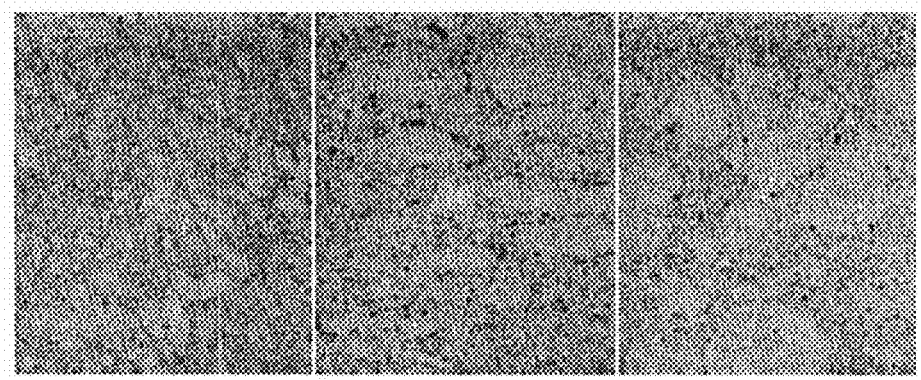
FIGS. 9A-9C. SS-31 reduced tubular cell apoptosis in obstructed kidney after UUO. Obstructed kidney from saline-treated animals (FIG. 9B); contralateral unobstructed control (FIG. 9A); obstructed kidney from SS-31 treated animals (FIG. 9C).

To determine whether SS-31 reduced tubular cell apoptosis in obstructed kidney after UUO, rats were treated with either saline (n=6) or SS-31 (1 mg/kg ip, n=6) one day prior to induction of UUO, and once a day for 14 days after UUO. Rats were then killed, kidneys removed, embedded in paraffin and sectioned. To quantitate nuclei with fragmented DNA, the TUNEL assay were performed with in situ TUNEL kit (Intergen, Purchase, N.Y.). Slides were developed with DAB and counterstained with 10% hematoxylin. The upregulation of CD36 in saline-treated controls associated with tubular cell apoptosis was significantly inhibited by SS-31 treatment (FIG. 9). Compared to the contralateral unobstructed control (FIG. 9A), a significant increase in apoptotic cells was observed in the obstructed kidney from saline-treated animals (FIG. 9B). The number of apoptotic cells was significantly reduced in obstructed kidney from SS-31 treated animals (FIG. 9C) ($P<0.001$; n=6).

Figures 10A, 10B, 10C:
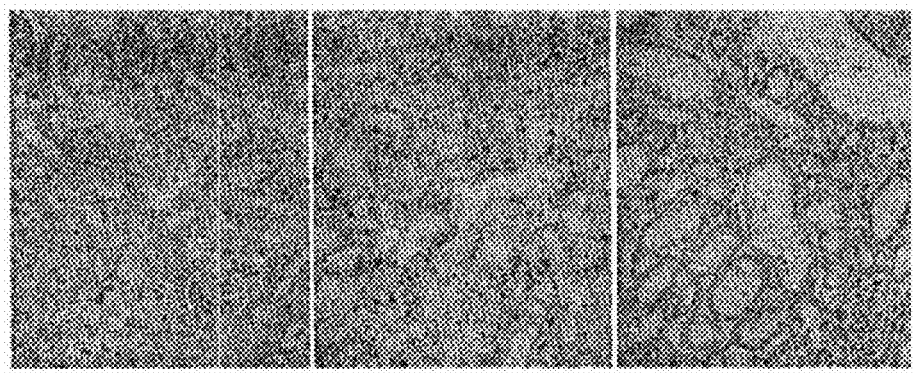
FIGS. 10A-10C. SS-31 reduced macrophage infiltration in obstructed kidney induced by UUO. Obstructed kidney (FIG. 10B); contralateral unobstructed control (FIG. 10A); rats treated with SS-31 (FIG. 10C).
Figures 11A, 11B, 11C:
FIGS. 11A-11C. SS-31 reduced interstitial fibrosis in obstructed kidney after UUO. Obstructed kidney (FIG. 11B); contralateral unobstructed control (FIG. 11A); rats treated with SS-31 (FIG. 11C).

Macrophage infiltration (FIG. 10) and interstitial fibrosis (FIG. 11) were also prevented by SS-31 treatment. Rats were treated with either saline (n=6) or SS-31 (1 mg/kg ip, n=6) one day prior to induction of UUO, and once a day for 14 days after UUO. Rats were then killed, kidneys removed, embedded in paraffin and sectioned. Slides were treated with monoclonal antibody for ED1 macrophage (1:75; Serotec). Horseradish-peroxidase-linked rabbit anti-mouse secondary antibody (Dako) was used for macrophage detection. Sections were then counterstained with 10% hematoxylin. The number of macrophages in the obstructed kidney in saline-treated rats (FIG. 10B) was significantly increased compared to the contralateral unobstructed control (FIG. 10A). Macrophage infiltration was significantly reduced in rats treated with SS-31 (FIG. 10C) ($P<0.05$; t-test).

Rats were treated with either saline (n=6) or SS-31 (1 mg/kg ip, n=6) one day prior to induction of UUO, and once a day for 14 days after UUO. Rats were then killed, kidneys removed, embedded in paraffin and sectioned. Slides were stained with hematoxylin and eosin and Masson's trichome for interstitial fibrosis (blue stain). Obstructed kidneys from saline-treated rats showed increase fibrosis (FIG. 11B) compared to the contralateral unobstructed control (FIG. 11A); while obstructed kidneys from SS-31 treated rats showed significantly less fibrosis ($P<0.05$; t-test).

These results show that SS-31 suppresses the upregulation of CD36 on renal tubular cells induced by UUO.

Example 6: SS-31 and SS-20 Reduced CD36 Expression in Isolated Hearts Upon Reperfusion after Prolonged Cold Ischemic Storage Organ transplantation requires hypothermic storage of the isolated organ for transport to the recipient. Currently, cardiac transplantation is limited by the short time of cold ischemic storage that can be tolerated before coronary blood flow is severely compromised (<4 hours). The expression of CD36 in coronary endothelium and cardiac muscles is up-regulated in isolated hearts subjected to prolonged cold ischemic storage and warm reperfusion.

Isolated guinea pig hearts were perfused with St. Thomas solution alone, or St. Thomas solution containing 1 nM SS-31 or 100 nM SS-20, for 3 min. and then stored in the same solution at 4° C. for 18 hours. After ischemic storage, hearts were reperfused with 34° C. Kreb-Henseleit solution for 90 min. Hearts freshly isolated from guinea pigs were used as controls.

Figures 12B, 12D, 12F, 12H, 12J:
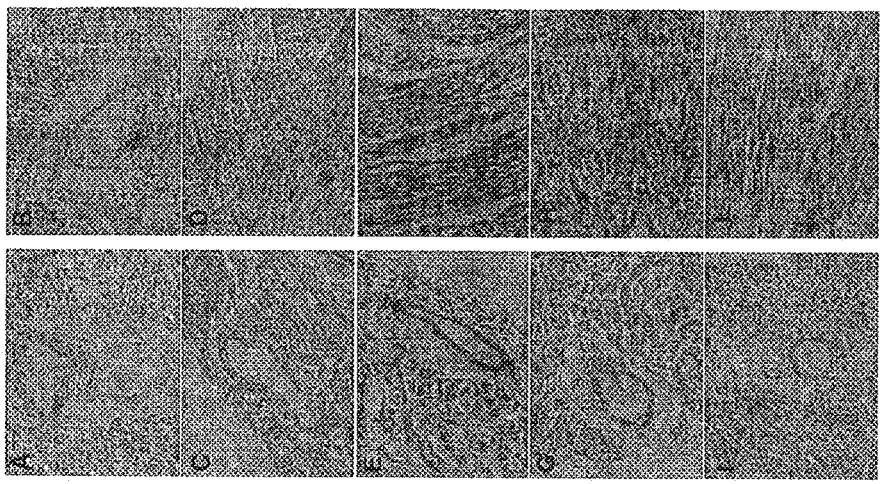

The hearts were fixed in paraffin and sliced for immunostaining with an anti-CD36 rabbit polyclonal antibody. The results are shown in FIG. 12. Two sections are shown for each treatment group. Antibody staining showed that CD36 is expressed in endothelium and cardiac muscles in normal hearts. The "background" (FIGS. 12A and 12B) represents two sections from a normal non-ischemic heart that was not treated with the primary antibody. "Normal heart" (FIGS. 12C and 12D) represents two sections obtained from a non-ischemic heart. The sections from a representative heart stored in St. Thomas solution (FIGS. 12E and 12F) for 18 hours at 4° C. showed increased CD36 staining compared to "Normal heart." CD36 staining was significantly reduced in hearts stored with either 1 nM SS-31 (FIGS. 12G and 12H) or 100 nM SS-20 (FIGS. 12I and 12J) in St. Thomas solution for 18 h.

CD36 staining is increased in hearts that have undergone 18 hours of cold ischemic storage and warm reperfusion. However, hearts that were stored with either 1 nM SS-31 or 100 nM SS-20 did not show the upregulation of CD36 expression.

Figure 13A:
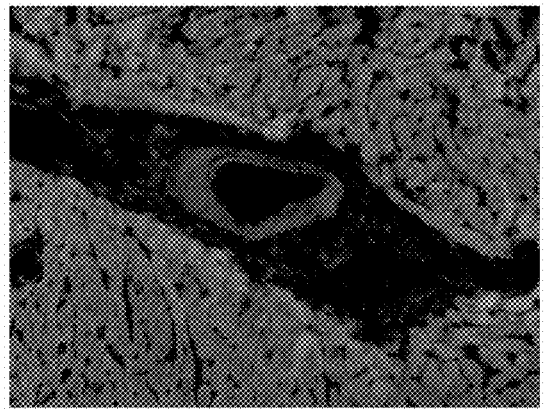
FIGS. 13A-13D. SS-31 and SS-20 reduced lipid peroxidation in isolated guinea pig hearts subjected to warm reperfusion after prolonged cold ischemia. HNE staining in hearts subjected to 18 hours of cold storage in St. Thomas solution (FIG. 13B) compared to non-ischemic hearts (FIG. 13A). HNE staining was reduced in hearts stored in SS-31 (FIG. 13C) or SS-20 (FIG. 13D).
Figure 13B:
Figure 13C:
Figure 13D:
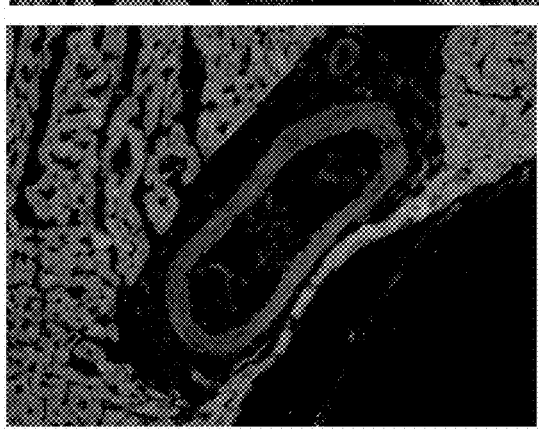

Lipid peroxidation in the hearts was also decreased by the aromatic-cationic peptides. Guinea pig hearts were perfused with a cardioplegic solution (St. Thomas solution) alone or St. Thomas solution containing either 1 nM SS-31 or 100 nM SS-20 for 3 min. and then subjected to 18 hours of cold ischemia (4° C.). The hearts were then reperfused with Krebs Henseleit buffer at 34° C. for 90 min. Immunohistochemical analysis of 4-hydroxynonenol (HNE)-modified proteins in paraffin sections from tissue slices were performed by incubation with an anti-HNE antibody (Santa Cruz) and a fluorescent secondary antibody. HNE staining was significantly increased in hearts subjected to 18 hours of cold storage in St. Thomas solution (FIG. 13B) compared to non-ischemic hearts (FIG. 13A). HNE staining was reduced in hearts stored in SS-31 (FIG. 13C) or SS-20 (FIG. 13D).

Further, the peptides dramatically reduced endothelial apoptosis (FIG. 14). Guinea pig heats were perfused with a cardioplegic solution (St. Thomas solution) alone or St. Thomas solution containing either 1 nM SS-31 or 100 nM SS-20 for 3 min. and then subjected to 18 hours of cold ischemia (4° C.). The hearts were then reperfused with Krebs Henseleit buffer at 34° C. for 90 min. After deparaffinization, sections were incubated with deoxynucleotidyl transferase (Tdt) with digoxigenin-dNTP for 1 hour. The reaction was stopped with terminating buffer. A fluorescent anti-digoxigenin antibody was then applied. Hearts subjected to 18 hours of cold storage in St. Thomas solution (FIGS. 14C and 14D) showed prominent endothelial apoptosis whereas no endothelial apoptosis was observed in non-ischemic normal hearts (FIGS. 14A and 14B). Apoptotic cells were not observed in hearts stored in SS-31 (FIGS. 14E and 14F) or SS-20 (FIGS. 14G and 14H).

Figure 15B:
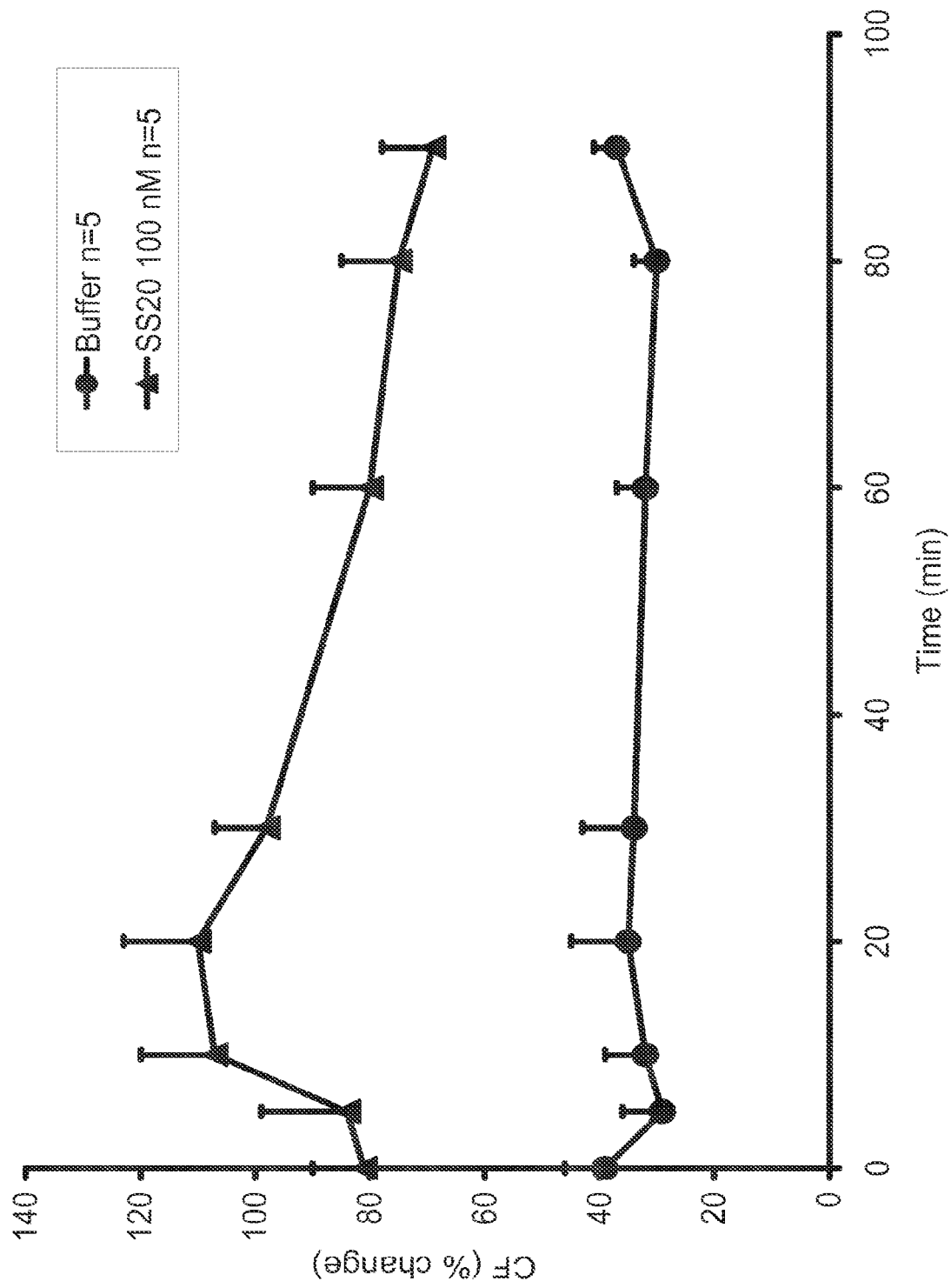

A significant improvement of coronary blood flow after prolonged cold ischemic storage and warm reperfusion occurred (FIG. 15). Guinea pigs hearts were perfused with a cardioplegic solution (St. Thomas solution) alone or St. Thomas solution containing either 1 nM SS-31 (FIG. 15A) or 100 nM SS-20) (FIG. 15B) for 3 min. and then subjected to 18 hours of cold ischemia (4° C.). The hearts were then reperfused with Krebs Henseleit buffer at 34° C. for 90 min. Coronary flow was significantly reduced after prolonged ischemia compared to pre-ischemic control (expressed as 100%). Preservation in either SS-31 or SS-20 significantly restored coronary flow to approximately 80% of pre-ischemic flow.

Example 7: SS-31 Prevented Renal Damage in Diabetic Mice

CD36 expression is upregulated in a variety of tissues of diabetic patients, including monocytes, heart, kidneys, and plasma. High glucose is known to upregulate the expression of CD36 by improving the translational efficiency of CD36 mRNA. Diabetic nephropathy is a common complication of type 1 and type 2 diabetes, and is associated with tubular epithelial degeneration and interstitial fibrosis. CD36 has been identified as a mediator of tubular epithelial apoptosis in diabetic nephropathy. High glucose stimulates CD36 expression and apoptosis in proximal tubular epithelial cells.

Streptozotocin (STZ) was used to induce diabetes in mice. Three groups of CD-1 mice were studied. Group I—no STZ treatment; Group II—STZ (50 mg/kg, ip) was given once a day for 5 d; Group III—STZ (50 mg/kg, ip) was given once a day for 5 d, and SS-31 (3 mg/kg, ip) was given once a day for 16 d. STZ treatment resulted in progressive increase in blood glucose. By week 3, blood glucose values were: Group I (10.6.noteq.0.27 mmol/L); Group II (24.5.noteq.1.15 mmol/L); Group III (21.3 1.48 mmol/L). Animals were sacrificed after 3 weeks and kidney tissues preserved for histopathology. Kidney sections were examined by Periodic Schiff (PAS) staining for renal tubular brush border.

STZ treatment caused dramatic loss of brush border in proximal tubules in the renal cortex (FIG. 16). In mice not treated with STZ, the renal brush border in the cortex was stained red with PAS (FIG. 16A, see white arrows). In mice treated with STZ, the brush border was obliterated, and the tubular epithelial cells showed small condensed nuclei (FIG. 16B). Daily treatment with SS-31 (3 mg/kg, ip) presented the loss of brush border in the STZ-treated mice (FIG. 16C), and the nuclei appeared normal (FIG. 16, top and bottom panels). In general, the architecture of the proximal renal tubules was preserved in diabetic mice treated with SS-31.

Figure 17A:
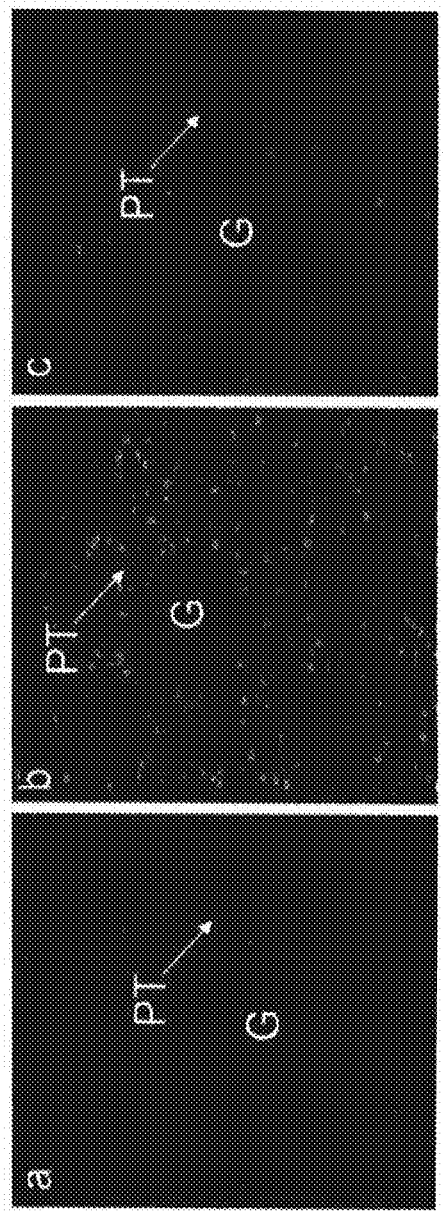
FIGS. 17A-17B. SS-31 prevented renal tubular epithelial cell apoptosis in diabetic mice. Diabetes was induced by streptozotocin (STZ) injection for 5 d. Kidney sections obtained after 3 weeks showed dramatic increase in apoptotic cells in proximal tubules in STZ-treated animals (FIG. 17A, panel b) that was not seen in mice not treated with STZ (FIG. 17A, panel a). The STZ-induced apoptosis was not seen in mice that received daily SS-31 (3 mg/kg) (FIG. 17A, panel c). The percent of apoptotic cells caused by STZ was significantly reduced by SS-31 treatment (FIG. 17B).
Figure 17B:
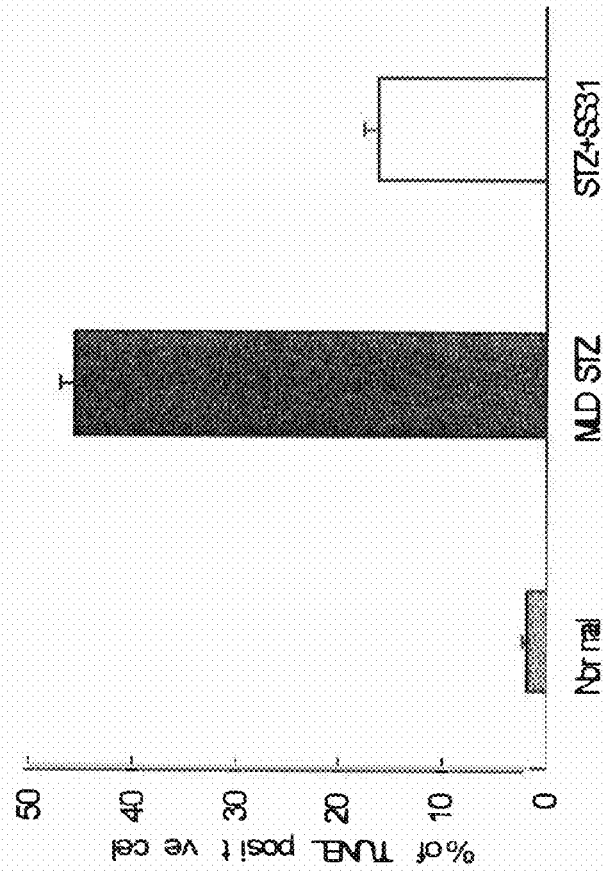

STZ treatment induced significant apoptosis in tubular epithelial cells (FIG. 17). Kidney sections were examined for apoptosis using the TUNEL assay. After deparaffinization, sections were incubated with deoxynucleotidyl transferase (Tdt) with digoxigenin-dNTP for 1 hour. The reaction was stopped with terminating buffer. A fluorescent anti-digoxigenin antibody was then applied. Kidney sections from mice treated with STZ showed large number of apoptotic nuclei in the proximal tubules (PT) (FIG. 17A, panel b), compared to no apoptotic cells in mice not treated STZ (FIG. 17A, panel a). Treatment with daily SS-31 dramatically reduced apoptotic cells in the proximal tubule (FIG. 17A, panel c). FIG. 17B shows the significant decrease in tubular cell apoptosis provided by SS-31.

CD36 expression in proximal tubular epithelial cells is known to be increased by high glucose and is upregulated in diabetic models. SS-31. by reducing CD36 expression, was able to inhibit tubular cell apoptosis and loss of brush border in mice treated with STZ without affecting blood glucose.

What is claimed is:

1. A method for treating diabetic neuropathy in a mammal in need thereof, the method comprising administering to the mammal an effective amount of an aromatic-cationic peptide having the formula D-Arg-2'6'-Dmt-Lys-Phe-NH$_2$ or Phe-D-Arg-Phe-Lys-NH$_2$.

2. The method of claim 1, wherein the mammal is a human.

3. The method of claim 1, wherein the mammal is suffering from type II diabetes.

4. The method of claim 1, wherein the peptide is administered orally, topically, systemically, intravenously, subcutaneously, or intramuscularly.

* * * * *